US007930104B2

(12) United States Patent
Baker et al.

(10) Patent No.: US 7,930,104 B2
(45) Date of Patent: Apr. 19, 2011

(54) PREDICTING RESPONSE TO CHEMOTHERAPY USING GENE EXPRESSION MARKERS

(75) Inventors: Joffre B. Baker, Montara, CA (US);
John L. Bryant, Allison Park, PA (US);
Soonmyung Paik, Pittsburgh, PA (US);
Steven Shak, Hillsborough, CA (US)

(73) Assignees: Genomic Health, Inc., Redwood City, CA (US); NSABP Foundation, Inc., Pittsburgh, PA (US)

( * ) Notice: Subject to any disclaimer, the term of this patent is extended or adjusted under 35 U.S.C. 154(b) by 1381 days.

(21) Appl. No.: 11/267,769

(22) Filed: Nov. 4, 2005

(65) Prior Publication Data

US 2006/0166230 A1    Jul. 27, 2006

Related U.S. Application Data

(60) Provisional application No. 60/625,485, filed on Nov. 5, 2004.

(51) Int. Cl.
C12Q 1/68 (2006.01)
G01N 33/48 (2006.01)
G06G 7/58 (2006.01)

(52) U.S. Cl. .................. 702/19; 435/6; 702/20; 703/11
(58) Field of Classification Search .......... None
See application file for complete search history.

(56) References Cited

U.S. PATENT DOCUMENTS

| | | | |
|---|---|---|---|
| 4,699,877 A | 10/1987 | Cline et al. | 435/6 |
| 4,968,603 A | 11/1990 | Slamon et al. | 435/6 |
| 5,015,568 A | 5/1991 | Tsujimoto et al. | 435/5 |
| 5,202,429 A | 4/1993 | Tsujimoto et al. | 536/23.5 |
| 5,459,251 A | 10/1995 | Tsujimoto et al. | 536/23.5 |
| RE35,491 E | 4/1997 | Cline et al. | 435/6 |
| 5,670,325 A | 9/1997 | Lapidus et al. | 435/6 |
| 5,741,650 A | 4/1998 | Lapidus et al. | 435/6 |
| 5,830,665 A | 11/1998 | Shuber et al. | 435/6 |
| 5,830,753 A | 11/1998 | Coulie et al. | 435/325 |
| 5,858,678 A | 1/1999 | Chinnadurai | 435/7.1 |
| 5,861,278 A | 1/1999 | Wong et al. | 435/69.1 |
| 5,928,870 A | 7/1999 | Lapidus et al. | 435/6 |
| 5,952,178 A | 9/1999 | Lapidus et al. | 435/6 |
| 5,952,179 A | 9/1999 | Chinnadurai | 435/6 |
| 5,962,312 A | 10/1999 | Plowman et al. | 435/320.1 |
| 5,985,553 A | 11/1999 | King et al. | 435/6 |
| 6,020,137 A | 2/2000 | Lapidus et al. | 435/6 |
| 6,100,029 A | 8/2000 | Lapidus et al. | 435/6 |
| 6,143,529 A | 11/2000 | Lapidus et al. | 435/91.2 |
| 6,146,828 A | 11/2000 | Lapidus et al. | 435/6 |
| 6,171,798 B1 | 1/2001 | Levine et al. | 435/6 |
| 6,203,993 B1 | 3/2001 | Shuber et al. | 435/6 |
| 6,207,401 B1 | 3/2001 | Plowman et al. | 435/15 |
| 6,207,452 B1 | 3/2001 | Govindaswamy | 435/330 |
| 6,214,558 B1 | 4/2001 | Shuber et al. | 435/6 |
| 6,245,523 B1 | 6/2001 | Altieri | 435/69.1 |
| 6,248,535 B1 | 6/2001 | Danenberg et al. | 435/6 |
| 6,271,002 B1 | 8/2001 | Linsley et al. | 435/91.1 |
| 6,322,986 B1 | 11/2001 | Ross | 435/6 |
| 6,414,134 B1 | 7/2002 | Reed | 536/24.5 |
| 6,582,919 B2 | 6/2003 | Danenberg | 435/6 |
| 6,602,670 B2 | 8/2003 | Danenberg | 435/6 |
| 6,618,679 B2 | 9/2003 | Loehrlein et al. | 702/20 |
| 6,620,606 B2 | 9/2003 | Bandman et al. | 435/219 |
| 6,696,558 B2 | 2/2004 | Reed et al. | 536/23.5 |
| 6,716,575 B2 | 4/2004 | Plowman et al. | 435/6 |
| 6,750,013 B2 | 6/2004 | Gish et al. | 435/6 |
| 6,800,737 B2 | 10/2004 | Altieri | 530/386 |
| 6,943,150 B1 | 9/2005 | Altieri | 514/21 |
| 2002/0004491 A1 | 1/2002 | Xu et al. | 514/44 |
| 2002/0009736 A1 | 1/2002 | Wang | 435/6 |
| 2002/0039764 A1 | 4/2002 | Rosen | 435/69.1 |
| 2002/0160395 A1 | 10/2002 | Altieri et al. | 435/6 |
| 2003/0073112 A1 | 4/2003 | Zhang et al. | 435/6 |
| 2003/0104499 A1 | 6/2003 | Pressman et al. | 435/7.23 |
| 2003/0165952 A1 | 9/2003 | Linnarsson et al. | 435/6 |
| 2003/0180791 A1 | 9/2003 | Chinnadurai | 435/6 |
| 2003/0198970 A1 | 10/2003 | Roberts | 435/6 |
| 2003/0198972 A1 | 10/2003 | Erlander et al. | 435/6 |
| 2003/0219771 A1 | 11/2003 | Bevilacqua et al. | 435/6 |
| 2003/0229455 A1 | 12/2003 | Bevilacqua et al. | 702/20 |
| 2004/0009489 A1 | 1/2004 | Golub et al. | 435/6 |
| 2004/0126775 A1 | 7/2004 | Altieri et al. | 435/6 |
| 2004/0133352 A1 | 7/2004 | Bevilacqua et al. | 702/19 |
| 2005/0048542 A1 | 3/2005 | Baker et al. | 435/6 |

FOREIGN PATENT DOCUMENTS

EP         0 108 564 B1    5/1988
(Continued)

OTHER PUBLICATIONS van't Veer et al., Nature, 2002, vol. 415, pp. 530-536.*
Cobleigh et al. Clinical Cancer Research, 2005, vol. 11, No. 24, pp. 8623.*
Ayers, M. et al., "Gene Expression Profiles Predict Complete Pathologic Response to Neoadjuvant Paclitaxel and Fluorouracil, Doxorubicin, and Cyclophosphamide Chemotherapy in Breast Cancer," *Journal of Clinical Oncology*, 22:(12), pp. 2284-2293, (2004).
Chang, J. et al., "Biologic Markers as Predictors of Clinical Outcome from Systemic Therapy for Primary Operable Breast Cancer," *Journal of Clinical Oncology*, 17:(10), pp. 3058-3063, (1999).

(Continued)

*Primary Examiner* — Shubo (Joe) Zhou
(74) *Attorney, Agent, or Firm* — Paula A. Borden; James S. Keddie; Bozicevic, Field & Francis LLP

(57) ABSTRACT

The present invention provides gene expression information useful for predicting whether a cancer patient is likely to have a beneficial response to treatment with chemotherapy, comprising measuring, in a biological sample comprising a breast tumor sample obtained from the patient, the expression levels of gene subsets to obtain a risk score associated with a likelihood of a beneficial response to chemotherapy, wherein the score comprises at least one of the following variables: (i) Recurrence Score, (ii) ESRI Group Score; (iii) Invasion Group Score; (iv) Proliferation Group Score; and (v) the expression level of the RNA transcript of at least one of MYBL2 and SCUBE2, or the corresponding expression product. The invention further comprises a molecular assay-based algorithm to calculate the likelihood that the patient will have a beneficial response to chemotherapy based on the risk score.

24 Claims, 2 Drawing Sheets

FOREIGN PATENT DOCUMENTS

| | | |
|---|---|---|
| EP | 1 365 034 | 11/2003 |
| WO | WO 99/02714 | 1/1999 |
| WO | WO 00/50595 | 8/2000 |
| WO | WO 00/55173 | 9/2000 |
| WO | WO 01/25250 | 4/2001 |
| WO | WO 01/40466 | 6/2001 |
| WO | WO 01/55320 | 8/2001 |
| WO | WO 01/70979 | 9/2001 |
| WO | WO 02/00677 | 1/2002 |
| WO | WO 02/06526 | 1/2002 |
| WO | WO 02/08260 | 1/2002 |
| WO | WO 02/08261 | 1/2002 |
| WO | WO 02/08282 | 1/2002 |
| WO | WO 02/08765 | 1/2002 |
| WO | WO 02/46467 | 6/2002 |
| WO | WO 02/017852 | 7/2002 |
| WO | WO 02/055988 | 7/2002 |
| WO | WO 02/059377 | 8/2002 |
| WO | WO 02/068579 | 9/2002 |
| WO | WO 02/103320 | 12/2002 |
| WO | WO 03/011897 | 2/2003 |
| WO | WO 03/078662 A1 | 9/2003 |
| WO | WO 03/083096 | 10/2003 |
| WO | WO 2004/046386 A1 | 6/2004 |

OTHER PUBLICATIONS

Garber, K., "Gene Expression Tests Foretell Breast Cancer's Future," *Science*, 303: pp. 1754-1755, (2004).

Paik, S. et al., "A Multigene Assay to Predict Recurrence of Tamoxifen-Treated, Node-Negative Breast Cancer," *The New England Journal of Medicine*, 351:(27), pp. 2817-2826, (2004).

Ravdin, P.M. et al., "Computer Program to Assist in Making Decisions about Adjuvant Therapy for Women with Early Breast Cancer," *Journal of Clinical Oncology*, 19:(4), pp. 980-991, (2001).

Brabender, Jan, et al.; *Epidermal Growth Factor Receptor and HER2-neu mRNA Expression in Non-Small Cell Lung Cancer Is Correlated with Survival*, Clinical Cancer Research; vol. 7, Jul. 2001; pp. 1850-1855.

Ding, Chunming, et al.; *A high-throughput gene expression analysis technique using competitive PCR and matrix-assisted laser desorption ionization time-of-flight MS*, PNAS, vol. 100:6; Mar. 18, 2003; pp. 3059-3064.

Cambridge Healthtech Institute Conference Agenda; "Enabling Molecular Profiling With Cellular Resolution: Microgenomics Using Homogeneous Cell Samples"; Dec. 2002; 5 pgs.

Yang, Li, et al.; *BADGE, BeadsArray for the Detection of Gene Expression, a High-Throughput Diagnostic Bioassay*; Genome Research; vol. 11; 2001; pp. 1888-1898.

Abba et al., Gene expression signature of estrogen receptor a status in breast cancer. BMC Genomics 2005; 6:37.

Bertucci et al., Gene expression profiling of primary breast carcinomas using arrays of candidate genes. Human Molecular Genetics 2000;9(20):2981-91.

Chenard et al., High levels of stromelysin-3 correlate with poor prognosis in patients with breast carcinoma. Int. J. Cancer (Pred. Oncol.) 1996; 69:448-451.

Engel et al., Correlation between Stromelysin-3 mRNA level and outcome of human breast cancer. Int. J. Cancer. 1994; 58:830-5.

Fisher et al., Relative worth of estrogen or progesterone receptor and pathologic characteristics of differentiation as indicators of prognosis in node negative breast cancer patients: Findings from national surgical adjuvant breast and bowel project protocol B-06. J. Clin. Oncology 1988; 6(7):1076-87.

Gasparini et al., Expression of bcl-2 protein predicts efficacy of adjuvant treatments in operable node-positive breast cancer. Clinical Cancer Research 1995; 1(189-190):189-98.

Glinsky et al., Microarray analysis identifies a death-from=cancer signature predicting therapy failure in patients with multiple types of cancer. J. Clin. Investigation 2005; 115(6):1503-21.

Kononen et al., Tissue microarrays for high-throughput molecular profiling of tumor specimens. Nature Medicine 1998; 4(7):844-7.

Lah et al., Cathepsin B, a prognostic indicator in lymph node-negative breast carcinoma patients: Comparison with cathespin D, cathespin L, and other clinical indicators. Clinical Cancer Research 2000: 6:578-84.

Miyoshi et al., Association of centrosomal kinase STK15/BTAK mRNA expression with chromosomal instability in human breast cancers. Int. J. Cancer 2001; 92:370-3.

Modlich et al., Predictors of primary breast cancers responsiveness to preoperative Epirubicin/Cyclophosphamide-based chemotherapy: translation of microarray data into clinically useful predictive signatures, J. Translational Medicine 2005: 3:32.

Nakopoulou et al., Stromelysin-3 protein expression in invasive breast cancer: Relation to proliferation, cell survival and patients' outcome. Modern Pathology 2002:15(11):1154-61.

Nessling et al., Candidate genes in breast cancer revealed by microarray-based comparative genomic hybridization of archived tissue. Cancer Res. 2005; 65(2):439-47.

Nishidate et al., Genome-wide gene-expression profiles of breast-cancer cells purified with laser microbeam microdissection: identification of genes associated with progression and metastasis. Int. J. Oncol. 2004.25(4):797-819.

Press et al., HER-2/neu gene amplification characterized by fluorescence in situ hybridization: Poor prognosis in node-negative breast carcinomas. J. Clin. Oncology 1997: 15(8):2894-904.

Reiner et al., Immunocytochemical localization of estrogen and progesterone receptor and prognosis in human primary breast cancer. Cancer Research 1990:50:7057-61.

Rundle et al., The association between glutathione S-transferase M1 genotype and polycyclic aromatic hydrocarbon-DNA adducts in breast tissue. Cancer Epidemiology, Biomarkers & Prevention 2000:9:1079-85.

Shen et al., Prognostic meta-signature of breast cancer developed by two-stage mixture modeling of microarray data. BMC Genomics 2004; 5:94.

Sorlie et al., Gene expression patterns of breast carcinomas distinguish tumor subclasses with clinical implications. PNAS 2001 ; 98(19):10869-74.

Span et al., Survivin is an independent prognostic marker for risk stratification of breast cancer patients. Clinical Chemistry 2004; 50(11):1986-93.

Stefano et al., Expression levels and clinical-pathological correlations of HER2/neu in primary and metastatic human breast cancer. Ann. N.Y. Acad. Sci. 2004; 1028:463-72.

Stein et al., The SH2 domain protein GRB-7 is co-amplified, overexpressed and in a tight complex with HER2 in breast cancer. EMBO Journal 1994; 13(6):1331-40.

Tanaka et al., Centrosomal kinase AIK1 is overexpressed in invasive ductal carcinoma of the breast. Cancer Research 1999; 59:2041-4.

Tanaka et al., Expression of survivin and its relationship to loss of apoptosis in breast carcinomas. Clinical Cancer Research 2000; 6:127-34.

Townsend et al., BAG-1 expression in human breast cancer: interrelationship between BAG-1 RNA, protein, HSC70 expression and clinico-pathological data. J Pathology 2002:197:51-59.

Turner et al., BAG-1: A novel biomarker predicting long-term survival in early stage breast cancer. J. Clin. Oncol. 2001;19(4):992-1000.

Valkovic et al., Correlation between vascular endothelial growth factor, angiogenesis, and tumor-associated macrophages in invasive ductal breast carcinoma. Virchows Arch. 2002:440:583-8.

Van De Vijver et al., A gene-expression signature as a predictor of survival in breast cancer. New Eng. J. Med. 2002; 347(25):1999-2009.

Van't Veer et al., Gene expression profiling predicts clinical outcome of breast cancer. Nature 2002; 415:530-6.

* cited by examiner

PREDICTING RESPONSE TO CHEMOTHERAPY USING GENE EXPRESSION MARKERS

This application claims priority under 35 U.S.C. §119(e) to provisional application Ser. No. 60/625,485 filed on Nov. 5, 2004, the entire disclosure of which is hereby expressly incorporated by reference.

FIELD OF THE INVENTION

The present invention provides gene expression information useful for predicting whether cancer patients are likely to have a beneficial response to treatment response with chemotherapy.

DESCRIPTION OF THE RELATED ART

Gene Expression Studies

Oncologists have a number of treatment options available to them, including different combinations of chemotherapeutic drugs that are characterized as "standard of care," and a number of drugs that do not carry a label claim for the treatment of a particular cancer, but for which there is evidence of efficacy in that cancer. Best likelihood of good treatment outcome requires that patients at highest risk of metastatic disease be identified and assigned to optimal available cancer treatment. In particular, it is important to determine the likelihood of patient response to "standard of care" therapeutic drugs, such as cyclophosphamide, methotrexate, 5-fluorouracil, anthracyclines, taxanes, and anti-estrogen drugs, such as tamoxifen, because these have limited efficacy and a spectrum of often severe side effects. The identification of patients who are most or least likely to need and respond to available drugs thus could increase the net benefit these drugs have to offer, and decrease net morbidity and toxicity, via more intelligent patient selection.

Currently, diagnostic tests used in clinical practice are single analyte, and therefore do not capture the potential value of knowing relationships between dozens of different markers. Moreover, diagnostic tests are often based on immunohistochemistry, which is not quantitative. Immunohistochemistry often yields different results in different laboratories primarily because the interpretations are subjective. RNA-based tests, while potentially highly quantitative, have not been developed because of the perception that RNA is destroyed in tumor specimens as routinely prepared, namely fixed in formalin and embedded in paraffin (FPE), and because it is inconvenient to obtain and store fresh tissue samples from patients for analysis.

Over the last two decades molecular biology and biochemistry have revealed hundreds of genes whose activities influence the behavior of tumor cells, their state of differentiation, and their sensitivity or resistance to certain therapeutic drugs. However, with a few exceptions, the status of these genes has not been exploited for the purpose of routinely making clinical decisions about drug treatments. In the last few years, several groups have published studies concerning the classification of various cancer types by microarray gene expression analysis of thousands of genes (see, e.g. Golub et al., *Science* 286:531-537 (1999); Bhattacharjae et al., Proc. Natl. Acad. Sci. USA 98:13790-13795 (2001); Chen-Hsiang et al., *Bioinformatics* 17 (Suppl. 1):S316-S322 (2001); Ramaswamy et al., *Proc. Natl. Acad. Sci. USA* 98:15149-15154 (2001); Martin et al., *Cancer Res.* 60:2232-2238 (2000); West et al., *Proc. Natl. Acad. Sci. USA* 98:11462-114 (2001); Sorlie et al., *Proc. Natl. Acad. Sci. USA* 98:10869-10874 (2001); Yan et al., *Cancer Res.* 61:8375-8380 (2001)). However, these studies have not yet yielded tests routinely used in clinical practice, in large part because microarrays require fresh or frozen tissue RNA and such specimens are not present in sufficient quantity to permit clinical validation of identified molecular signatures.

In the past three years, it has become possible to profile gene expression of hundreds of genes in formalin-fixed paraffin-embedded (FPE) tissue using RT-PCR technology. Methods have been described that are sensitive, precise, and reproducible (Cronin et al., *Am. J. Pathol.* 164:35-42 (2004)). Because thousands of archived FPE clinical tissue specimens exist with associated clinical records, such as survival, drug treatment history, etc., the ability to now quantitatively assay gene expression in this type of tissue enables rapid clinical studies relating expression of certain genes to patient prognosis and likelihood of response to treatments. Using data generated by past clinical studies allows for rapid results because the clinical events are historical. In contrast, for example, if one wished to carry out a survival study on newly recruited cancer patients one would generally need to wait for many years for statistically sufficient numbers of deaths to have occurred.

Breast Cancer

Breast cancer is the most common type of cancer among women in the United States, and is the leading cause of cancer deaths among women ages 40-59.

Currently only a few molecular tests are routinely used clinically in breast cancer. Immunohistochemical assays for estrogen receptor (ESR1) and progesterone receptor (PGR) proteins are used as a basis for selection of patients to treatment with anti-estrogen drugs, such as tamoxifen (TAM). In addition, ERBB2 (Her2) immunochemistry or fluorescence in situ hybridization (which measure protein and DNA, respectively) are used to select patients with the Her2 antagonist drugs, such as trastuzumab (Herceptin®; Genentech, Inc., South San Francisco, Calif.).

Because current tests for prognosis and for prediction of response to chemotherapy are inadequate, breast cancer treatment strategies vary between oncologists (Schott and Hayes, *J. Clin. Oncol.* PMID 15505274 (2004); Hayes, *Breast* 12:543-9 (2003)). Generally, lymph node negative patients whose tumors are found to be ESR1 positive are treated with an anti-estrogen drug, such as TAM, and patients whose tumors are found to be ESR1 negative are treated with chemotherapy. Often, ESR1 positive are also prescribed chemotherapy in addition to anti-estrogen therapy, accepting the toxic side effects of chemotherapy in order to modestly decrease the risk of cancer recurrence. Toxicities include, neuropathy, nausea and other gastrointestinal symptoms, hair loss and cognitive impairment. Recurrence is to be feared because recurrent breast cancer is usually metastatic and poorly responsive to treatment. Clearly, a need exists to identify those patients who are at substantial risk of recurrence (i.e., to provide prognostic information) and likely to respond to chemotherapy (i.e., to provide predictive information). Likewise, a need exists to identify those patients who do not have a significant risk of recurrence, or who are unlikely to respond to chemotherapy, as these patients should be spared needless exposure to these toxic drugs.

Prognostic factors differ from treatment predictive factors in breast cancer. Prognostic factors are those variables related to the natural history of breast cancer, which influence the recurrence rates and outcome of patients once they have developed breast cancer. Clinical parameters that have been associated with a worse prognosis include, for example, lymph node involvement, increasing tumor size, and high grade tumors. Prognostic factors are frequently used to categorize patients into subgroups with different baseline relapse risks. In contrast, treatment predictive factors are variables related to the likelihood of an individual patient's beneficial response to a treatment, such as anti-estrogen or chemotherapy, independent of prognosis.

There is a great need for accurate, quantitative tests that reliably predict the likelihood of a cancer patient, such as a breast cancer patient, to a certain type of treatment. Such tests would assist the practicing physician to make intelligent treatment choices, adapted to a particular patient's needs, based on well founded risk-benefit analysis.

SUMMARY OF THE INVENTION

Figure 1:
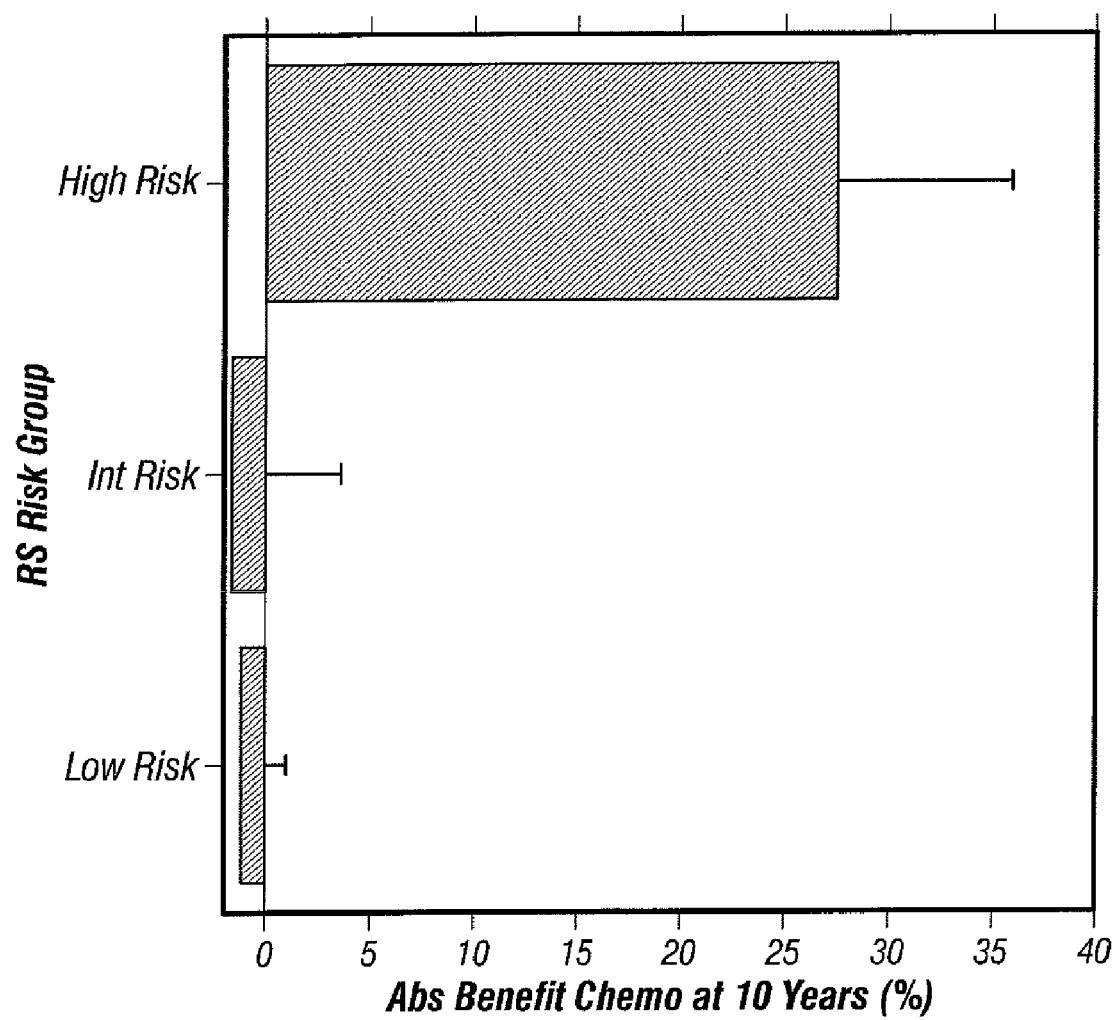
FIG. 1 shows the absolute benefit of chemotherapy as determined by DRFS at 10 years within NSABP B-20 patient groups identified by Recurrence Score as low, intermediate or high risk.

In one aspect, the invention concerns a method for predicting the likelihood of a beneficial response to chemotherapy of a subject diagnosed with cancer, comprising
(a) quantitatively determining, in a biological sample comprising cancer cells obtained from said subject, the value of one or more of the following variables:
  (i) Recurrence Score,
  (ii) ESR1 Group Score;
  (iii) Invasion Group Score;
  (iv) Proliferation Group Threshold Score; and
  (v) the expression level of the RNA transcript of at least one of MYBL2 and SCUBE2, or the corresponding expression product,
  wherein
(b1) for every unit of an increase in the value of one or more of (i), (iii), (iv), or the expression level of the RNA transcript of MYBL2, or the corresponding expression product, said subject is identified to have a proportionately increased likelihood of a beneficial response to said chemotherapy; and
(b2) for every unit of an increase in the value of (ii) or the expression level of the RNA transcript of SCUBE2, or the corresponding expression product, said subject is identified to have a proportionately decreased likelihood of a beneficial response to chemotherapy; and
(b3) for every unit of an increase in the value of (i), said subject is identified as having an increased likelihood of a beneficial response to chemotherapy, as measured by a reduced risk of breast cancer recurrence;
wherein ESR1 Group Score=(ESR1+PGR+BCL2+SCUBE2)/4;

Invasion Group Score=(CTSL2+MMP11)/2;

GRB7 Group Score=0.9×GRB7+0.1×ERBB2;

GRB7 Group Threshold Score equals 8 if the GRB7 Group Score is less than 8 and equals the GRB7 Group Score if the GRB7 Group Score is 8 or more Proliferation Group Score=(BIRC5+MKI67+MYBL2+CCNB1+STK6)/5;

Proliferation Group Threshold Score equals 6.5, if the Proliferation Group Score is less than 6.5; and equals the Proliferation Group Score, if the Proliferation Group Score is 6.5 or more, and $$RS = \begin{cases} 0 & \text{if } 20 \times (RS_U - 6.7) < 0 \\ 20 \times (RS_U - 6.7) & \text{if } 0 \le 20 \times (RS_U - 6.7) \le 100 \\ 100 & \text{if } 20 \times (RS_U - 6.7) > 100 \end{cases}$$

wherein
  $RS_u$=0.47×GRB7 Group Threshold Score
    −0.34×ESR1 Group Score
    +1.04×Proliferation Group Threshold Score
    +0.10×Invasion Group Score
    +0.05×CD68
    −0.08×GSTM1
    −0.07×BAG1
where the gene symbols in the equations represent the expression levels of the RNA transcripts of the respective genes, or their expression products, and the individual contributions of the genes in variables (i), (ii), (iii), and (iv) are weighted by a factor between 0.5 to 1.5; and
wherein every individual gene and every gene present in any of said variables can be substituted by another gene that coexpresses with said gene in said cancer with a Pearson correlation coefficient of $\ge 0.5$.

The subject preferably is a mammal, including primates, such as a human patient.

In a particular embodiment, the expression levels of all genes included in variables (i)-(v), or their expression products, are normalized relative to the expression levels of one or more reference genes, or their expression products. For example, the reference genes can be selected from the group consisting of ACTB, GAPD, GUSB, RPLP0, and TFRC. In another embodiment, the expression levels are normalized relative to the mean of the expression levels of ACTB, GAPD, GUSB, RPLP0, and TFRC, or their expression products.

In a further embodiment, the quantitative value of the likelihood of a beneficial response to chemotherapy is directly proportional to the value of the variable or variables determined over a continuum.

The cancer can, for example, be a solid tumor, such as breast cancer, ovarian cancer, gastric cancer, colon cancer, pancreatic cancer, prostate cancer, and lung cancer. The breast cancer includes, without limitation, invasive breast cancer, or stage II or stage III breast cancer, and ESR1 positive breast cancer.

When the patient is determined to have an increased likelihood of a beneficial response to chemotherapy, the method of the invention may additionally include a step of treating the patient with chemotherapy. Chemotherapy can be adjuvant or neoadjuvant chemotherapy, and includes the administration of any chemotherapeutic drug that has been shown effective for the treatment of the particular cancer. Thus, chemotherapeutic drugs include anthracycline derivatives, such as doxorubicin or adriamycin; taxane derivatives, such as paclitaxel or docetaxel; topoisomerase inhibitors, such as camptothecin, topotecan, irinotecan, 20-S-camptothecin, 9-nitro-camptothecin, 9-amino-camptothecin, or GI147211; and inhibitors of nucleotide biosynthesis, such as methotrexate and/or 5-fluorouracil (5-FU).

The method of the invention may comprise the determination of at least two, or at least three, or at least four, or five of the listed variables.

In a particular embodiment, the method of the invention comprises determination of the expression level of one or both of MYBL2 and SCUBE2, or their expression products.

The biological sample may, for example, be a tissue sample comprising cancer cells.

The tissue sample can be, without limitation, fixed, paraffin-embedded, or fresh, or frozen, and can be derived, for example, from fine needle, core, or other types of biopsy. In a particular embodiment, the tissue sample is obtained by fine needle aspiration, bronchial lavage, or transbronchial biopsy.

In a further embodiment, determination of the expression levels includes quantitative RT-PCR.

In a different embodiment, determination of the expression levels of the expression products of the listed genes includes immunohistochemistry.

In a further embodiment, the levels of the gene expression products are determined by proteomics techniques.

In a still further embodiment, the expression levels of the genes are determined by quantitative RT-PCR, using primer and probe sequences based on a target gene sequence.

In a specific embodiment, at least one target gene sequence is an intron-based sequence, the expression of which correlates with the expression of an exon sequence of the same gene.

The method of the present invention may include a step of creating a report summarizing said likelihood of beneficial response, and optionally a step of providing the report to a patient diagnosed with cancer and/or the patient's physician as a personalized genomic profile.

In another aspect, the invention concerns a method of preparing a personalized genomics profile for a subject diagnosed with cancer, comprising (a) quantitatively determining, in a biological sample comprising cancer cells obtained from said subject, the value of one or more of the following variables:
 (i) Recurrence Score,
 (ii) ESR1 Group Score;
 (iii) Invasion Group Score;
 (iv) Proliferation Group Threshold Score; and
 (v) the expression level of the RNA transcript of at least one of MYBL2 and SCUBE2,
 wherein
(b1) for every unit of an increase in the value of one or more of (i), (iii), (iv), or the expression level of the RNA transcript of MYBL2, or the corresponding expression product, said subject is identified to have a proportionately increased likelihood of a beneficial response to said chemotherapy;
(b2) for every unit of an increase in the value of (ii) or the expression level of the RNA transcript of SCUBE2, or the corresponding expression product, said subject is identified to have a proportionately decreased likelihood of a beneficial response to chemotherapy; and
(b3) for every unit of an increase in the value of (i) said subject is identified as having an increased likelihood of breast cancer recurrence in the absence of chemotherapy;
wherein $ESR1$ Group Score=$(0.8 \times ESR1 + 1.2 \times PGR + BCL2 + SCUBE2)/4$;

Invasion Group Score=$(CTSL2 + MMP11)/2$;

$GRB7$ Group Score=$0.9 \times GRB7 + 0.1 \times ERBB2$;

GRB7 Group Threshold Score equals 8 if the GRB7 Group Score is less than 8 and equals the GRB7 Group Score if the GRB7 Group Score is 8 or more.

Proliferation Group Score=$(BIRC5 + MKI67 + MYBL2 + CCNB1 + STK6)/5$;

Proliferation Group Threshold Score equals 6.5, if the Proliferation Group Score is less than 6.5; and is identical with the Proliferation Group Score, if the Proliferation Group Score is 6.5 or more, and $$RS = \begin{cases} 0 & \text{if } 20 \times (RS_U - 6.7) < 0 \\ 20 \times (RS_U - 6.7) & \text{if } 0 \leq 20 \times (RS_U - 6.7) \leq 100 \\ 100 & \text{if } 20 \times (RS_U - 6.7) > 100 \end{cases}$$

wherein
 $RS_U$=0.47×GRB7 Group Threshold Score
  −0.34×ESR1 Group Score
  +1.04×Proliferation Group Threshold Score
  +0.10×Invasion Group Score
  +0.05×CD68
  −0.08×GSTM1
  −0.07×BAG1 where the gene symbols in the equations represent the expression levels of the RNA transcripts of the respective genes, or their expression products, and the individual contributions of the genes in variables (i), (ii), (iii), and (iv) can be weighted by a factor between 0.5 to 1.5; and wherein every individual gene or gene present in any of said variables can be substituted by another gene that coexpresses with said gene in said cancer with a Pearson's coefficient of ≧0.5; and (c) creating a report summarizing the data obtained by the gene expression analysis.

In a specific embodiment, if an increase in the value of one or more of (i), (iii), (iv), or the expression level of the RNA transcript of MYBL2, or the corresponding expression product, is determined, the report includes a prediction that the subject has an increased likelihood of a beneficial response to chemotherapy. In this case, the method may further include the step of treating said subject with a chemotherapeutic agent.

In yet another embodiment, if an increase in the value of (ii) or the expression level of the RNA transcript of SCUBE2, or the corresponding expression product, is determined, the report includes a prediction that the subject has a decreased likelihood of a beneficial response to chemotherapy.

DETAILED DESCRIPTION OF THE PREFERRED EMBODIMENT

A. Definitions

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994); and Webster's New World™ Medical Dictionary, 2nd Edition, Wiley Publishing Inc., 2003, provide one skilled in the art with a general guide to many of the terms used in the present application. For purposes of the present invention, the following terms are defined below.

The term "microarray" refers to an ordered arrangement of hybridizable array elements, preferably polynucleotide probes, on a substrate.

The term "polynucleotide," when used in singular or plural, generally refers to any polyribonucleotide or polydeoxribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The term "gene expression" describes the conversion of the DNA gene sequence information into transcribed RNA (the initial unspliced RNA transcript or the mature mRNA) or the encoded protein product. Gene expression can be monitored by measuring the levels of either the entire RNA or protein products of the gene or their subsequences.

The term "over-expression" with regard to an RNA transcript is used to refer to the level of the transcript determined by normalization to the level of reference mRNAs, which might be all measured transcripts in the specimen or a particular reference set of mRNAs.

The phrase "gene amplification" refers to a process by which multiple copies of a gene or gene fragment are formed in a particular cell or cell line. The duplicated region (a stretch of amplified DNA) is often referred to as "amplicon." Usually, the amount of the messenger RNA (mRNA) produced, i.e., the level of gene expression, also increases in the proportion of the number of copies made of the particular gene expressed.

Prognostic factors are those variables related to the natural history of breast cancer, which influence the recurrence rates and outcome of patients once they have developed breast cancer. Clinical parameters that have been associated with a worse prognosis include, for example, lymph node involvement, increasing tumor size, and high grade tumors. Prognostic factors are frequently used to categorize patients into subgroups with different baseline relapse risks. In contrast, treatment predictive factors are variables related to the likelihood of an individual patient's beneficial response to a treatment, such as anti-estrogen or chemotherapy, independent of prognosis.

The term "prognosis" is used herein to refer to the likelihood of cancer-attributable death or cancer progression, including recurrence and metastatic spread of a neoplastic disease, such as breast cancer, during the natural history of the disease. Prognostic factors are those variables related to the natural history of a neoplastic diseases, such as breast cancer, which influence the recurrence rates and disease outcome once the patient developed the neoplastic disease, such as breast cancer. In this context, "natural outcome" means outcome in the absence of further treatment. For example, in the case of breast cancer, "natural outcome" means outcome following surgical resection of the tumor, in the absence of further treatment (such as, chemotherapy or radiation treatment). Prognostic factors are frequently used to categorize patients into subgroups with different baseline risks, such as baseline relapse risks.

The term "prediction" is used herein to refer to the likelihood that a patient will respond either favorably or unfavorably to a drug or set of drugs, and also the extent of those responses. Thus, treatment predictive factors are those variables related to the response of an individual patient to a specific treatment, independent of prognosis. The predictive methods of the present invention can be used clinically to make treatment decisions by choosing the most appropriate treatment modalities for any particular patient. The predictive methods of the present invention are valuable tools in predicting if a patient is likely to respond favorably to a treatment regimen, such as anti-estrogen therapy, such as TAM treatment alone or in combination with chemotherapy and/or radiation therapy.

The term "beneficial response" means an improvement in any measure of patient status including those measures ordinarily used in the art such as overall survival, long-term survival, recurrence-free survival, and distant recurrence-free survival. Recurrence-free survival (RFS) refers to the time (in years) from surgery to the first local, regional, or distant recurrence. Distant recurrence-free survival (DFRS) refers to the time (in years) from surgery to the first distant recurrence. Recurrence refers to RFS and/or DFRS as evidenced by its particular usage. The calculation of these measures in practice may vary from study to study depending on the definition of events to be either censored or not considered. The term "long-term" survival is used herein to refer to survival for at least 3 years, more preferably for at least 8 years, most preferably for at least 10 years following surgery or other treatment.

The term "tumor," as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include, but are not limited to, breast cancer, ovarian cancer, colon cancer, lung cancer, prostate cancer, hepatocellular cancer, gastric cancer, pancreatic cancer, cervical cancer, liver cancer, bladder cancer, cancer of the urinary tract, thyroid cancer, renal cancer, carcinoma, melanoma, and brain cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

In the context of the present invention, reference to "at least one," "at least two," "at least three," "at least four," "at least five," etc. of the genes listed in any particular gene set means any one or any and all combinations of the genes listed.

The term "node negative" cancer, such as "node negative" breast cancer, is used herein to refer to cancer that has not spread to the draining lymph nodes.

The terms "splicing" and "RNA splicing" are used interchangeably and refer to RNA processing that removes introns and joins exons to produce mature mRNA with continuous coding sequence that moves into the cytoplasm of an eukaryotic cell.

In theory, the term "exon" refers to any segment of an interrupted gene that is represented in the mature RNA product (B. Lewin. *Genes IV* Cell Press, Cambridge Mass. 1990). In theory the term "intron" refers to any segment of DNA that is transcribed but removed from within the transcript by splicing together the exons on either side of it. Operationally, exon sequences occur in the mRNA sequence of a gene as defined by Ref. SEQ ID numbers. Operationally, intron sequences are the intervening sequences within the genomic DNA of a gene, bracketed by exon sequences and having GT and AG splice consensus sequences at their 5' and 3' boundaries.

B. Detailed Description

The practice of the present invention will employ, unless otherwise indicated, conventional techniques of statistical analysis, molecular biology (including recombinant techniques), microbiology, cell biology, and biochemistry, which are within the skill of the art. Such techniques are explained fully in the literature, such as, "Molecular Cloning: A Laboratory Manual", $2^{nd}$ edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", $4^{th}$ edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); "Statistical Methods and Scientific Inference", 3 editions (R. A. Fisher., 1956/59/74) and "PCR: The Polymerase Chain Reaction", (Mullis et al., eds., 1994).

B.1. General Description of the Invention

Over the past two years Genomic Health, Inc and collaborators (Esteban et al., *Proc Am Soc Clin Oncol* 22: page 850, 2003 (abstract 3416); Soule et al., *Proc Am Soc Clin Oncol* 22: page 862, 2003 (abstract 3466); Cobleigh et al. *Soc Clin Oncol* 22: page 850, 2003 (abstract 3415); Cronin et al., *Am J Pathol* 164(1):35-42 (2004)) reported several exploratory clinical studies of gene expression in early breast cancer, aimed at finding a molecular signature for recurrence risk. These studies used quantitative RT-PCR to test 250 candidate gene markers in frozen, paraffin-embedded (FPE) tissue specimens having linked clinical records. Analysis across all three studies was performed in order to examine whether genes could be identified which were consistently related to the risk of recurrence across a diverse group of patients. Based on these univariate results, multi-gene models were designed and analyzed across the three studies. A single multi-gene assay, consisting of 16 cancer-related genes and 5 reference genes, was developed to be tested prospectively in clinical validation studies. An algorithm called Recurrence Score (RS) was generated, which utilizes the measurements of these 21 mRNA species and reports recurrence risk on a 100 point scale.

To test the clinical validity of this Recurrence Score test and algorithm, a blinded clinical trial with prospectively identified endpoints was carried out. This validation trial focused on patients treated with TAM alone in the randomized and registration arms of the NSABP Study B-14 clinical trial population (Fisher B, Costantino J P, Redmond C K, et al: Endometrial cancer in -treated breast cancer patients: Findings from the National Surgical Adjuvant Breast and Bowel Project (NSABP) B-14. *J Natl Cancer Inst* 86:527-537 (1994)). Genomic Health, Inc. and the NSABP carried out the 21 gene RT-PCR assay on 668 breast cancer tissue specimens derived from these patients and calculated a Recurrence Score for each patient.

Pre-specified cut-off points of Recurrence Score classified patients into one of three categories: low risk, intermediate risk, and high risk of distant disease recurrence. The proportion of the 668 patients categorized as low, intermediate, and high risk by the RT-PCR assay were 51%, 23%, and 27%, respectively. The Kaplan-Meier estimates and 95% confidence intervals for the rates of distant recurrence at 10 years were 6.8% (4.0%, 9.6%), 14.3% (8.3%, 20.3%) 30.5% (23.6%, 37.4%), respectively, for the low, intermediate, and high risk groups; the rate for the low risk group was significantly lower than the rate for the high risk group (p<0.001). In a multivariate Cox model relating distant recurrence to Recurrence Score, age, and tumor size, Recurrence Score provides significant (p<0.001) predictive power that goes beyond age and tumor size. This study validated the Recurrence Score as a powerful predictor of distant recurrence in patients without involved nodes who have tumors that are ESR1 positive and treated with tamoxifen (Paik et al. Breast Cancer Research and Treatment 82, Supplement 1: page S10, 2003 (Abstract 16).

In expanding the results of these findings, and using the results of NSABP Study B-20, the present invention provides genes and gene sets useful in predicting the response of cancer, e.g., breast cancer, patients to chemotherapy. In addition, the invention provides a clinically validated test, predictive of breast cancer patient response to chemotherapy, using multi-gene RNA analysis.

In particular, the present inventors identified a set of genes: BCL2; SCUBE2; CCNB1; CTSL2; ESR1; MMP11; MYBL2; PGR; STK6; BIRC5 and MMP11, GSTM1, CD68; BAG1; GRB7; ERBB2, which are useful in predicting whether a cancer patient, such as a breast cancer patient is likely to show a beneficial response to chemotherapy. Some of these genes are predictive individually, while others are used as part of certain gene groups, used as variables in the methods of the present invention.

Thus, the independent variables used in the predictive methods of the present invention include one or more of (i) Recurrence Score, (ii) ESR1 Group Score; (iii)

Invasion Group Score; (iv) Proliferation Group Threshold Score; and (v) the expression level of the RNA transcript of at least one of MYBL2 and SCUBE2,
   wherein
     (b1) for every unit of an increase in the value of one or more of (i), (iii), (iv), or the expression level of the RNA transcript of MYBL2, or the corresponding expression product, the patient is identified to have a proportionately increased likelihood of a beneficial response to chemotherapy;

(b2) for every unit of an increase in the value of (ii) or the expression level of the RNA transcript of SCUBE2, or the corresponding expression product, the patient is identified to have a proportionately decreased likelihood of a beneficial response to chemotherapy; and (b3) for every unit of an increase in the value of (i), the patient is identified as having an increased likelihood of breast cancer recurrence in the absence of chemotherapy.

In the above variables:

$ESR1 \text{ Group Score} = (ESR1 + PGR + BCL2 + SCUBE2)/4;$ $\text{Invasion Group Score} = (CTSL2 + MMP11)/2;$ $\text{Proliferation Group Score} = (BIRC5 + MMP11 + MYBL2 + CCNB1 + STK6)/5;$ Proliferation Group Threshold Score equals 6.5, if the Proliferation Group Score is less than 6.5; and is identical with the Proliferation Group Score, if the Proliferation Group Score is 6.5 or more, and Recurrence Score (RS):

$$RS = \begin{cases} 0 & \text{if } 20 \times (RS_U - 6.7) < 0 \\ 20 \times (RS_U - 6.7) & \text{if } 0 \le 20 \times (RS_U - 6.7) \le 100 \\ 100 & \text{if } 20 \times (RS_U - 6.7) > 100 \end{cases}$$

wherein $GRB7 \text{ Group Score} = 0.9 \times GRB7 + 0.1 \times ERBB2$

GRB7 Group Threshold Score equals 6.5, if the GRB7 Group Score is less than 6.5; and is identical with the GRB7 Group Score, if the GRB7 Group Score is 6.5 or more, and $RS_U = 0.47 \times GRB7 \text{ Group Threshold Score} - 0.34 \times ESR1 \text{ Group Score} +$
$1.04 \times \text{Proliferation Group Threshold Score} +$
$0.10 \times \text{Invasion Group Score} +$
$0.05 \times CD68 - 0.08 \times GSTM1 - 0.07 \times BAG1$ where the gene symbols in the equations represent the expression levels of the RNA transcripts of the respective genes, or their expression products, and the individual contributions of the genes in variables (i), (ii), (iii), and (iv) can be weighted by a factor between 0.5 to 1.5; and where every individual gene or gene present in any of said variables can be substituted by another gene that coexpresses with said gene in said cancer with a Pearson coefficient of $\geq 0.5$ and where any gene that coexpresses with said individual gene or gene present in any of said variables, can be added to the respective gene Group and be used to calculate the respective variable, wherein the denominator used in the calculation of the Group score is equal to the number of genes in the group. The addition of a gene that coexpresses with said individual gene may cause the formation of a new Group, which likewise can be weighted by a factor between 0.5 to 1.5.

In various embodiments of the inventions, various technological approaches are available for determination of expression levels of the disclosed genes, including, without limitation, RT-PCR, microarrays, serial analysis of gene expression (SAGE) and Gene Expression Analysis by Massively Parallel Signature Sequencing (MPSS), which will be discussed in detail below. In particular embodiments, the expression level of each gene may be determined in relation to various features of the expression products of the gene including exons, introns, protein epitopes and protein activity.

B.2 Gene Expression Profiling

In general, methods of gene expression profiling can be divided into two large groups: methods based on hybridization analysis of polynucleotides, and methods based on sequencing of polynucleotides. The most commonly used methods known in the art for the quantification of mRNA expression in a sample include northern blotting and in situ hybridization (Parker & Barnes, Methods in Molecular Biology 106:247-283 (1999)); RNAse protection assays (Hod, Biotechniques 13:852-854 (1992)); and reverse transcription polymerase chain reaction (RT-PCR) (Weis et al., Trends in Genetics 8:263-264 (1992)). Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

Two biological processes commonly involved in tumorigenesis include gene amplification and DNA methylation. Both processes result in the abnormal expression of genes important in tumor formation or progression. Methods that monitor gene amplification and DNA methylation can therefore be considered surrogate methods for gene expression profiling.

Gene amplification is a common alteration in many cancers that can lead to elevated expression of cellular oncogenes (Meltzer, P. et al., Cancer Genet Cytogenet. 19:93 (1986). In breast cancer, there is good correlation between ERBB2 gene amplification and ERBB2 overexpression (Nagai, M. A. et al., Cancer Biother 8:29 (1993), Savinainen, K. J. et al., Am. J. Pathol. 160:339 (2002)). Amplification of the ERBB2 gene, leading to its overexpression, correlates with poor prognosis (Press, M. F. et al., J. Clin. Oncol. 15:2894 (1997), Slamon, D. J. et al., Science 244:707 (1989)) and is predictive for response to anti-HER2 therapy in combination with standard chemotherapy(Seidman, A. D. et al., J. Clin. Oncol. 19:1866 (2001)).

DNA methylation has also been shown to be a common alteration in cancer leading to elevated or decreased expression of a broad spectrum of genes (Jones, P. A. Cancer Res. 65:2463 (1996)). In general, hypomethylation of CpG islands in the promoter regions and regulatory elements results in increased gene expression, including many oncogenes (Hanada, M., et al., Blood 82:1820 (1993), Feinberg, A. P. and Vogelstein, B. Nature 301:89 (1983)). Because DNA methylation correlates with the level of specific gene expression in many cancers, it serves as a useful surrogate to expression profiling of tumors (Toyota, M. et al., Blood 97: 2823 (2001), Adoijan, P. et al. Nucl. Acids. Res. 10:e21 (2002)).

Reverse Transcriptase PCR (RT-PCR)

Of the techniques listed above, the most sensitive and most flexible quantitative method is RT-PCR, which can be used to compare mRNA levels in different sample populations, in normal and tumor tissues, with or without drug treatment, to characterize patterns of gene expression, to discriminate between closely related mRNAs, and to analyze RNA structure.

The first step is the isolation of mRNA from a target sample. The starting material is typically total RNA isolated from human tissues or cell lines. Thus RNA can be isolated from a variety of primary tumors, including breast, lung, colon, prostate, brain, liver, kidney, pancreas, spleen, thymus, testis, ovary, uterus, etc., or tumor cell lines. If the source of mRNA is a primary tumor, mRNA can be extracted, for example, from frozen or archived paraffin-embedded and fixed (e.g. formalin-fixed) tissue samples.

General methods for mRNA extraction are well known in the art and are disclosed in standard textbooks of molecular biology, including Ausubel et al., *Current Protocols of Molecular Biology*, John Wiley and Sons (1997). Methods for RNA extraction from paraffin embedded tissues are disclosed, for example, in Rupp and Locker, *Lab Invest.* 56:A (1987), and De Andres et al., *BioTechniques* 18:42044 (1995). In particular, RNA isolation can be performed using purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include Master-Pure™ Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

As RNA cannot serve as a template for PCR, the first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, CA, USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TaqMan® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, ABI PRISM 7700™ Sequence Detection System™ (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700™ Sequence Detection System™. The system consists of a thermocycler, laser, charge-coupled device (CCD), camera and computer. The system amplifies samples in a 96-well format on a thermocycler. During amplification, laser-induced fluorescent signal is detected at the CCD. The system includes software for running the instrument and for analyzing the data.

5'-Nuclease assay data are initially expressed as $C_T$, or the threshold cycle. As discussed above, fluorescence values are recorded during every cycle and represent the amount of product amplified to that point in the amplification reaction. The point when the fluorescent signal is first recorded as statistically significant is the threshold cycle ($C_T$).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPD) and β-actin (ACTB).

A more recent variation of the RT-PCR technique is the real time quantitative PCR, which measures PCR product accumulation through a dual-labeled fluorigenic probe (i.e., TaqMan® probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., *Genome Research* 6:986-994 (1996).

The steps of a representative protocol for profiling gene expression using fixed, paraffin-embedded tissues as the RNA source, including mRNA isolation, purification, primer extension and amplification are given in various published journal articles {for example: T. E. Godfrey et al. J. Molec. Diagnostics 2: 84-91 [2000]; K. Specht et al., Am. J. Pathol. 158: 419-29 [2001]}. Briefly, a representative process starts with cutting about 10 μm thick sections of paraffin-embedded tumor tissue samples. The RNA is then extracted, and protein and DNA are removed. After analysis of the RNA concentration, RNA repair and/or amplification steps may be included, if necessary, and RNA is reverse transcribed using gene specific promoters followed by RT-PCR.

Microarrays

Differential gene expression can also be identified, or confirmed using the microarray technique. Thus, the expression profile of breast cancer-associated genes can be measured in either fresh or paraffin-embedded tumor tissue, using microarray technology. In this method, polynucleotide sequences of interest (including cDNAs and oligonucleotides) are plated, or arrayed, on a microchip substrate. The arrayed sequences are then hybridized with specific DNA probes from cells or tissues of interest. Just as in the RT-PCR method, the source of mRNA typically is total RNA isolated from human tumors or tumor cell lines, and corresponding normal tissues or cell lines. Thus RNA can be isolated from a variety of primary tumors or tumor cell lines. If the source of mRNA is a primary tumor, mRNA can be extracted, for example, from frozen or archived paraffin-embedded and fixed (e.g. formalin-fixed) tissue samples, which are routinely prepared and preserved in everyday clinical practice.

In a specific embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., *Proc. Natl. Acad. Sci. USA* 93(2):106-149 (1996)). Microarray analysis can be performed by commercially available equipment, following manufacturer's protocols, such as by using the Affymetrix GenChip technology, or Incyte's microarray technology.

The development of microarray methods for large-scale analysis of gene expression makes it possible to search systematically for molecular markers of cancer classification and outcome prediction in a variety of tumor types.

Serial Analysis of Gene Expression (SAGE)

Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et al., *Science* 270:484-487 (1995); and Velculescu et al., *Cell* 88:243-51 (1997).

Gene Expression Analysis by Massively Parallel Signature Sequencing (MPSS)

This method, described by Brenner et al., *Nature Biotechnology* 18:630-634 (2000), is a sequencing approach that combines non-gel-based signature sequencing with in vitro cloning of millions of templates on separate 5 µm diameter microbeads. First, a microbead library of DNA templates is constructed by in vitro cloning. This is followed by the assembly of a planar array of the template-containing microbeads in a flow cell at a high density (typically greater than $3\times10^6$ microbeads/cm$^2$). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast cDNA library.

General Description of the mRNA Isolation, Purification and Amplification

The steps of a representative protocol for profiling gene expression using fixed, paraffin-embedded tissues as the RNA source, including mRNA isolation, purification, primer extension and amplification are provided in various published journal articles (for example: T. E. Godfrey et al,. *J. Molec. Diagnostics* 2: 84-91 [2000]; K. Specht et al., *Am. J. Pathol.* 158: 419-29 [2001]). Briefly, a representative process starts with cutting about 10 µm thick sections of paraffin-embedded tumor tissue samples. The RNA is then extracted, and protein and DNA are removed. After analysis of the RNA concentration, RNA repair and/or amplification steps may be included, if necessary, and RNA is reverse transcribed using gene specific promoters followed by RT-PCR. Finally, the data are analyzed to identify the best treatment option(s) available to the patient on the basis of the characteristic gene expression pattern identified in the tumor sample examined, dependent on the predicted likelihood of cancer recurrence.

Breast Cancer Gene Set, Assayed Gene Subsequences, and Clinical Application of Gene Expression Data An important aspect of the present invention is to use the measured expression of certain genes by breast cancer tissue to provide prognostic or predictive information. For this purpose it is necessary to correct for (normalize away) both differences in the amount of RNA assayed and variability in the quality of the RNA used. Therefore, the assay typically measures and incorporates the expression of certain normalizing genes, including well known housekeeping genes, such as ACTB, GAPD, GUSB, RPLO, and TFRC, as shown in the Example below. Alternatively, normalization can be based on the mean or median signal ($C_T$) of all of the assayed genes or a large subset thereof (global normalization approach). Below, unless noted otherwise, gene expression means normalized expression.

Design of Intron-Based PCR Primers and Probes

According to one aspect of the present invention, PCR primers and probes are designed based upon intron sequences present in the gene to be amplified. Accordingly, the first step in the primer/probe design is the delineation of intron sequences within the genes. This can be done by publicly available software, such as the DNA BLAT software developed by Kent, W. J., *Genome Res* 12(4):656-64 (2002), or by the BLAST software including its variations. Subsequent steps follow well established methods of PCR primer and probe design.

In order to avoid non-specific signals, it is important to mask repetitive sequences within the introns when designing the primers and probes. This can be easily accomplished by using the Repeat Masker program available on-line through the Baylor College of Medicine, which screens DNA sequences against a library of repetitive elements and returns a query sequence in which the repetitive elements are masked. The masked intron sequences can then be used to design primer and probe sequences using any commercially or otherwise publicly available primer/probe design packages, such as Primer Express (Applied Biosystems); MGB assay-by-design (Applied Biosystems); Primer3 (Steve Rozen and Helen J. Skaletsky (2000) Primer3 on the WWW for general users and for biologist programmers. In: Krawetz S, Misener S (eds) *Bioinformatics Methods and Protocols: Methods in Molecular Biology*. Humana Press, Totowa, N.J., pp 365-386).

The most important factors considered in PCR primer design include primer length, melting temperature (Tm), and G/C content, specificity, complementary primer sequences, and 3'-end sequence. In general, optimal PCR primers are generally 17-30 bases in length, and contain about 20-80%, such as, for example, about 50-60% G+C bases. Tm's between 50 and 80° C., e.g. about 50 to 70° C. are typically preferred.

For further guidelines for PCR primer and probe design see, e.g. Dieffenbach, C. W. et al., "General Concepts for PCR Primer Design" in: *PCR Primer, A Laboratory Manual*, Cold Spring Harbor Laboratory Press, New York, 1995, pp. 133-155; Innis and Gelfand, "Optimization of PCRs" in: *PCR Protocols, A Guide to Methods and Applications*, CRC Press, London, 1994, pp. 5-11; and Plasterer, T. N. Primerselect: Primer and probe design. *Methods Mol. Biol.* 70:520-527 (1997), the entire disclosures of which are hereby expressly incorporated by reference.

B.3 Algorithms and Statistical Methods

The present invention takes advantage of certain algorithms and statistical methods, which are described in copending application Ser. No. 10/883,303.

When quantitative RT-PCR (qRT-PCR) is used to measure mRNA levels, mRNA amounts are expressed in $C_T$ (threshold cycle) units (Held et al., *Genome Research* 6:986-994 (1996)). The averaged sum of reference mRNA $C_T$s is set at some number, for example, zero, and each measured test mRNA $C_T$ is given relative to this point. For example, if, for a certain patient tumor specimen the average of $C_T$s of the 5 reference genes is found to be 31 and $C_T$ of the test gene X is found to be 35, the reported value for gene X is −4 (i.e. 31-35).

As a first step following the quantitative determination of mRNA levels, the genes identified in the tumor specimen and known to be associated with the molecular pathology of cancer are grouped into subsets. Thus, genes known to be associated with cell proliferation will constitute the "Proliferation Group" (axis, or subset). Genes known to be associated with invasion by the cancer of adjacent tissue will constitute the "Invasion Group" (axis, or subset). Genes associated with key growth factor receptor signaling pathway(s) will constitute the "Growth Factor Group" (axis, or subset), also referred to as GRB7 group. Genes known to be involved with activating or signaling through the estrogen receptor (ESRI) will constitute the "Estrogen Receptor (ESRI) Group" (axis, or subset), and so on. This list of subsets is, of course, not limiting. The subsets created will depend on the particular cancer, i.e. breast, prostate, pancreatic, lung, etc. cancer. In general, genes the expression of which is known to correlate with each other, or which are known to be involved in the same pathway are grouped in the same subset.

In the next step, the measured tumor level of each mRNA in a subset is multiplied by a coefficient reflecting its relative intra-set contribution to the risk of cancer recurrence to obtain a product, and this product is added to the other products similarly calculated using mRNA levels in the subset and their coefficients, to yield a term, e.g. a proliferation term, an invasion term, a growth factor term, etc. For example, in the case of lymph node-negative invasive breast cancer the growth factor (GRB7 Group) term is (0.45 to 1.35)×GRB7+ (0.05 to 0.15)×ERBB2, such as, for example 0.9×GRB7+ 0.1×ERBB2 (see Example below).

The contribution of each term to the overall recurrence score is weighted by use of an additional coefficient. For example, in the case of lymph node-negative invasive breast cancer the coefficient of the GRB7 Group term can be between 0.23 and 0.70.

Additionally, for some terms, such as the growth factor and proliferation terms, a further step is performed. If the relationship between the term and the risk of recurrence is non-linear, a non-linear functional transform of the term, such as a threshold is used.

The sum of the terms obtained provides the recurrence score (RSu), which predicts the likelihood of cancer recurrence in the normal course of the disease.

The RS scale generated by the algorithm of the present invention can be adjusted in various ways. Thus, the range could be selected such that the scale run from 0 to 10, 0 to 50, or 0 to 100, for example.

For example, in the particular scaling approach described in the Example below, scaled recurrence score is calculated on a scale of 0 to 100. For convenience, 10 is added to each measured $C_T$ value, and unscaled RS is calculated as described before. Equations for calculating RS and SRS are provided in the following Example.

In calculating the recurrence score, or any variable used to calculate the recurrence score, any gene can be substituted by another gene that coexpresses with the first gene in the particular cancer tested with a Pearson's coefficient of $\geq 0.5$. Similarly, any individual gene, or gene within a gene group (subset) included in the prognostic and predictive methods of the present invention can be substituted by another gene that coexpresses with the first gene in the particular cancer tested with a Pearson's coefficient of $\geq 0.5$.

B.4 Cancer Chemotherapy

Chemotherapeutic agents used in cancer treatment can be divided into several groups, depending on their mechanism of action. Some chemotherapeutic agents directly damage DNA and RNA. By disrupting replication of the DNA such chemotherapeutics either completely halt replication, or result in the production of nonsense DNA or RNA. This category includes, for example, cisplatin (Platinol®), daunorubicin (Cerubidine®), doxorubicin (Adriamycin®), and etoposide (VePesid®). Another group of cancer chemotherapeutic agents interfere with the formation of nucleotides or deoxyribonucleotides, so that RNA synthesis and cell replication is blocked. Examples of drugs in this class include methotrexate (Abitrexate®), mercaptopurine (Purinethol®), fluorouracil (Adrucil®), and hydroxyurea (Hydrea®). A third class of chemotherapeutic agents effects the synthesis or breakdown of mitotic spindles, and, as a result, interrupt cell division. Examples of drugs in this class include Vinblastine (Velban®), Vincristine (Oncovin®) and taxenes, such as, Paclitaxel (Taxol®), and Tocetaxel (Taxotere®) Tocetaxel is currently approved in the United States to treat patients with locally advanced or metastatic breast cancer after failure of prior chemotherapy, and patients with locally advanced or metastatic non-small cell lung cancer after failure of prior platinum-based chemotherapy. The prediction of patient response to all of these, and other chemotherapeutic agents is specifically within the scope of the present invention.

In a specific embodiment, chemotherapy includes treatment with a taxane derivative. Taxanes include, without limitation, paclitaxel (Taxol®) and docetaxel (Taxotere®), which are widely used in the treatment of cancer. As discussed above, taxanes affect cell structures called microtubules, which play an important role in cell functions. In normal cell growth, microtubules are formed when a cell starts dividing. Once the cell stops dividing, the microtubules are broken down or destroyed. Taxanes stop the microtubules from breaking down, which blocks cell proliferation.

In another specific embodiment, chemotherapy includes treatment with an anthracycline derivative, such as, for example, doxorubicin, daunorubicin, and aclacinomycin.

In a further specific embodiment, chemotherapy includes treatment with a topoisomerase inhibitor, such as, for example, camptothecin, topotecan, irinotecan, 20-S-camptothecin, 9-nitro-camptothecin, 9-amino-camptothecin, or GI147211.

Treatment with any combination of these and other chemotherapeutic drugs is specifically contemplated.

Most patients receive chemotherapy immediately following surgical removal of the tumor. This approach is commonly referred to as adjuvant therapy. However, chemotherapy can be administered also before surgery, as so called neoadjuvant treatment. Although the use of neo-adjuvant chemotherapy originates from the treatment of advanced and inoperable breast cancer, it has gained acceptance in the treatment of other types of cancers as well. The efficacy of neo-adjuvant chemotherapy has been tested in several clinical trials. In the multi-center National Surgical Adjuvant Breast and Bowel Project B-18 (NSAB B-18) trial (Fisher et al., *J. Clin. Oncology* 15:2002-2004 (1997); Fisher et al., *J. Clin. Oncology* 16:2672-2685 (1998)) neoadjuvant therapy was performed with a combination of adriamycin and cyclophosphamide ("AC regimen"). In another clinical trial, neoadjuvant therapy was administered using a combination of 5-fluorouracil, epirubicin and cyclophosphamide ("FEC regimen") (van Der Hage et al., *J. Clin. Oncol.* 19:4224-4237 (2001)). Newer clinical trials have also used taxane-containing neoadjuvant treatment regiments. See, e.g. Holmes et al., *J. Natl. Cancer Inst.* 83:1797-1805 (1991) and Moliterni et al., *Seminars in Oncology*, 24:S17-10-S-17-14 (1999). For further information about neoadjuvant chemotherapy for breast cancer see, Cleator et al., *Endocrine-Related Cancer* 9:183-195 (2002).

B.5 Kits of the Invention

The materials for use in the methods of the present invention are suited for preparation of kits produced in accordance with well known procedures. The invention thus provides kits comprising agents, which may include gene-specific or gene-selective probes and/or primers, for quantitating the expression of the disclosed genes for predicting prognostic outcome or response to treatment. Such kits may optionally contain reagents for the extraction of RNA from tumor samples, in particular fixed paraffin-embedded tissue samples and/or reagents for RNA amplification. In addition, the kits may optionally comprise the reagent(s) with an identifying description or label or instructions relating to their use in the methods of the present invention. The kits may comprise containers (including microtiter plates suitable for use in an automated implementation of the method), each with one or more of the various reagents (typically in concentrated form) utilized in the methods, including, for example, pre-fabricated microarrays, buffers, the appropriate nucleotide triphosphates (e.g., dATP, dCTP, dGTP and dTTP; or rATP, rCTP, rGTP and UTP), reverse transcriptase, DNA polymerase, RNA polymerase, and one or more probes and primers of the present invention (e.g., appropriate length poly(T), gene specific or random primers linked to a promoter reactive with the RNA polymerase).

The methods provided by the present invention may also be automated in whole or in part.

All aspects of the present invention may also be practiced such that a limited number of additional genes that are co-expressed with the disclosed genes, for example as evidenced by high Pearson correlation coefficients, are included in a prognostic or predictive tests in addition to and/or in place of disclosed genes.

Having described the invention, the same will be more readily understood through reference to the following Example, which is provided by way of illustration, and is not intended to limit the invention in any way.

EXAMPLE

A Study of Adjuvant Chemotherapy in Invasive Breast Cancer: Gene Expression Profiling of Paraffin-Embedded Core Biopsy Tissue This study was carried out to identify genes or gene groups that predict patient sensitivity or resistance to chemotherapy. The study utilized tissue and data from NSABP Study B-20: "A Clinical Trial to Determine the Worth of Chemotherapy and Tamoxifen over Tamoxifen Alone in the Management of Patients with Primary Invasive Breast Cancer, Negative Axillary Nodes and Estrogen-Receptor-Positive Tumors." Fisher et al., *J Natl Cancer Inst* 89(22):1673-1682 (1997).

Study Design

Patient inclusion criteria: Enrolled in NSABP Study B-20. Patient exclusion criteria: No tumor block available from initial diagnosis in the NSABP archive; no tumor or very little tumor in block as assessed by examination of the H&E slide by pathologist; insufficient RNA (<275 ng) for RT-PCR analysis; average non-normalized CT for the 5 reference genes <35; clinical ineligible or without follow-up.

Laboratory Assay

Fixed, paraffin-embedded breast tumor tissue specimens from up to 600 patients who were treated at study entry with TAM plus chemotherapy in the B-20 study were analyzed. RNA previously extracted from fixed paraffin embedded breast tumor tissue from up to 252 patients who were treated at study entry with TAM alone in the B-20 study was reanalyzed. The expression of 16 cancer-related genes and 5 reference genes was quantitatively assessed for each patient using TaqMan® RT-PCR, which was performed in triplicate with RNA input at 2 ng per reaction.

The gene expression algorithm that was prospectively defined prior to RT-PCR analysis of the tumor tissue in this study was used to calculate a Recurrence Score for each patient.

Pathology Review and Preparation

Group 1: Cases with no tumor or very little tumor (<5% of the area occupied by invasive cancer cells compared to the area occupied by other epithelial elements, such as normal epithelium, fibrocystic change, or DCIS/LCIS) were excluded from the study.

Group 2: Cases with regions on the slide having prominent non-tumor elements (such as smooth muscle, hemorrhage, fibrosis, hyperplastic, epithelium, and/or normal breast; but not DCIS, LCIS or necrosis) where the non-tumor elements were both sufficiently localized to be amenable to macro-dissection and sufficiently abundant (>50% of the overall tissue on the slide). Macro-dissection was performed on these cases.

Group 3: All other cases were analyzed without dissection.

Patient Survival

For the primary analysis, distant recurrence-free survival (DRFS) was based on the time (in years) from surgery to first distant recurrence. Contralateral disease, other second primary cancers, and deaths prior to distant recurrence were considered censoring events.

Gene Expression

Expression levels of 21 genes used in the calculation of the Recurrence Score were reported as values from the GHI assay. Table 1 gives the identities of 16 test and 5 reference genes. Gene expression values were normalized relative to the mean of the 5 reference genes. The reference genes are known to be relatively invariant in breast cancer as well as under various sample and process conditions, making them useful for normalizing for extraneous effects. Reference-normalized expression measurements typically range from 0 to 15, where a one unit increase generally reflects a 2-fold increase in RNA quantity. The 21 pre-specified genes for analysis are listed in Table 1.

TABLE 1

Gene Expression Panel

| Cancer-Related Genes/ Accession Number | | Reference Genes/ Accession Number | |
|---|---|---|---|
| BAG1 | NM_004323 | ACTB | NM_001101 |
| BCL2 | NM_000633 | GAPD | NM_002046 |
| CCNB1 | NM_031966 | GUSB | NM_000181 |
| CD68 | NM_001251 | RPLP0 | NM_001002 |
| SCUBE2 | NM_020974 | TFRC | NM_003234 |
| CTSL2 | NM_001333 | | |
| ESR1 | NM_000125 | | |
| GRB7 | NM_005310 | | |
| GSTM1 | NM_000561 | | |
| ERBB2 | NM_004448 | | |
| MMP11 | NM_002417 | | |
| MYBL2 | NM_002466 | | |
| PGR | NM_000926 | | |
| STK6 | NM_003600 | | |
| MMP11 | NM_005940 | | |
| BIRC5 | NM_001168 | | |

Biostatistical Analysis

The Recurrence Score contains both prognostic and predictive factors. For the purpose of identifying treatment predictive genes in breast cancer, the primary objective was to explore the relation between gene expression and DRFS in treated patients. For such analyses, data from both treated and untreated patients were utilized in order to discriminate treatment predictive genes from purely prognostic genes. For identifying chemotherapy treatment predictive genes, both patients treated with TAM only and patients treated with both TAM and chemotherapy were included from the NSABP Study B-20.

Cox proportional hazards models were utilized to examine the interaction between the treatment effect and gene expression Cox, *J Royal Stat Soc* Series B 34(2): 187-220 (1972); Themeau and Gramsch, *Modeling Survival Data: Extending the Cox Model*, Springer, New York, N.Y. (2000) ISBN 0-387-98784-3. An interaction between treatment and gene expression exists if the treatment effect depends on the gene expression level; that is, if gene expression is a treatment predictive factor (Fisher, *Statistical Methods and Scientific Inference*, Oliver and Boyd, Edinburgh (1974); Savage *The foundations of Statisitics*, John Wiley, New York (1964). The likelihood ratio test was used to identify statistically significant predictive treatment genes by comparing the reduced model excluding the gene expression by treatment interaction versus the competing full model including the gene expression by treatment interaction.

Recurrence Score

The Recurrence Score (RS) on a scale from 0 to 100 is derived from the reference-normalized expression measurements as follows:

$RSu = 0.47 \times GRB7$ Group Threshold Score $- 0.34 \times ESR1$ Group Score $+$ $1.04 \times$ Proliferation Group Threshold Score $+$ $0.10 \times$ Invasion Group Score $+$ $0.05 \times CD68 - 0.08 \times GSTM1 - 0.07 \times BAG1$ where:

$GRB7$ Group Score$=0.9 \times GRB7 + 0.1 \times ERBB2$ $GRB7$ Group Threshold Score $=$ $$\begin{cases} 8 & \text{If } GRB7 \text{ Group Score} < 8 \\ GRB7 \text{ Group Score} & \text{Otherwise} \end{cases}$$

$ESR1$ Group Score$=(\times Esrt1+\times PGR+BCL2+SCUBE2)/4$

Proliferation Group Score$=(BIRC5+MKI67+MYBL2+CCNB1+STK6)/5$

Proliferation Group Threshold Score $=$ $$\begin{cases} 6.5 & \text{If Prolif. Group Score} < 6.5 \\ \text{Proliferation Group Score} & \text{Otherwise} \end{cases}$$

Invasion Group Score$=(CTSL2+MMP11)/2$

The $RS_u$ (Recurrence Score unscaled) is then rescaled to be between 0 and 100:

$$RS = \begin{cases} 0 & \text{if } 20 \times (RS_U - 6.7) < 0 \\ 20 \times (RS_U - 6.7) & \text{if } 0 \leq 20 \times (RS_U - 6.7) \leq 100 \\ 100 & \text{if } 20 \times (RS_U - 6.7) > 100 \end{cases}$$

Classification into Three Groups

The RS was used to determine a recurrence risk group for each patient. The cut-off points between the low, intermediate, and high risk recurrence groups will be defined as follows:

| Risk Group | Recurrence Score |
|---|---|
| Low risk of recurrence | Less than 18 |
| Intermediate risk of recurrence | Greater than or equal to 18 and less than 31 |
| High risk of recurrence | Greater than or equal to 31 |

Results

Table 2 shows that six of the tested variables interacted with beneficial chemotherapy response, as measured by 10-year DRFS, with statistical significance (P<0.1), namely RS, Proliferation Group Threshold Score (ProlThres), MYBL2, Invasion Group Score, SCUBE2, and ESR1 Group Score. The interaction analysis for RS was carried out over the lower half of the total 100 point range, as indicated by the RS/50 term in Table 2.

TABLE 2

Interaction Analysis

| Variable | Estimate | P-value | H.R. | 95% CI for H.R. | |
|---|---|---|---|---|---|
| IntRS/50 | −1.151 | 0.038 | 0.316 | 0.107 | 0.936 |
| IntProlThres | −1.12114 | 0.038 | 0.325 | 0.112 | 0.943 |
| IntMYBL2 | −0.4043 | 0.049 | 0.667 | 0.445 | 0.999 |
| IntInvasionGoup | −0.64788 | 0.055 | 0.523 | 0.269 | 1.016 |
| IntSCUBE2 | 0.221844 | 0.062 | 1.248 | 0.988 | 1.577 |
| IntESR1Group | 0.279682 | 0.093 | 1.322 | 0.953 | 1.834 |

As shown in Table 2, increased expression of the following genes and gene sets correlates with increased likelihood of 10-year distant recurrence-free survival: RS; MYBL2; Proliferation Group Threshold Score; Invasion Group Score. Increased expression of the following genes correlates with decreased likelihood of beneficial response to treatment: SCUBE2; ESR1 Group Score. It is noteworthy that individual key components of the RS algorithm, namely ProlifAxisthresh, InvasionGroup, and ESR1 Group all independently influence response to chemotherapy in a direction in accord with rise in RS corresponding to increased likelihood of chemotherapy benefit.

FIG. 1 shows the relationship between RS risk group category (low, intermediate, and high risk) and percent benefit of chemotherapy across the NSABP B-20 population at 10 years. Average benefit among high risk patients (defined by RS>31) was about 28%, with 95% confidence limits spanning 12-42%. That is, in this group on average chemotherapy decreased the absolute risk of recurrence at 10 years by 28%. This is remarkable because high risk patients without chemotherapy on average have an absolute risk of recurrence of a little over 30%, indicating that chemotherapy can reduce the relative rate of recurrence by around 90% in this patient group. In the case of intermediate risk patients (defined by RS between 18 and 31) average benefit was nearly zero, with 95% confidence limits spanning −10 to +10%. In the case of low risk patients (defined by RS<18) average benefit was nearly zero, with 95% confidence limits spanning −4 to +4%.

These results have utility for guiding the decision about whether to treat an ESR1 positive early breast cancer patient with chemotherapy. The validation of the Recurrence Score algorithm in the NSABP B14 TAM treatment arm demonstrated that patients in the high risk group have a >30% risk of breast cancer recurrence at 10 years. The data presented here indicate that this high risk population has very substantial benefit from chemotherapy treatment if they choose to take it, potentially reducing recurrence to that of low risk patients. On the other hand, the TAM-treated low risk population, which has a risk of recurrence without chemotherapy of ~7%, can expect chemotherapy to produce relatively little reduction in risk.

Figure 2:
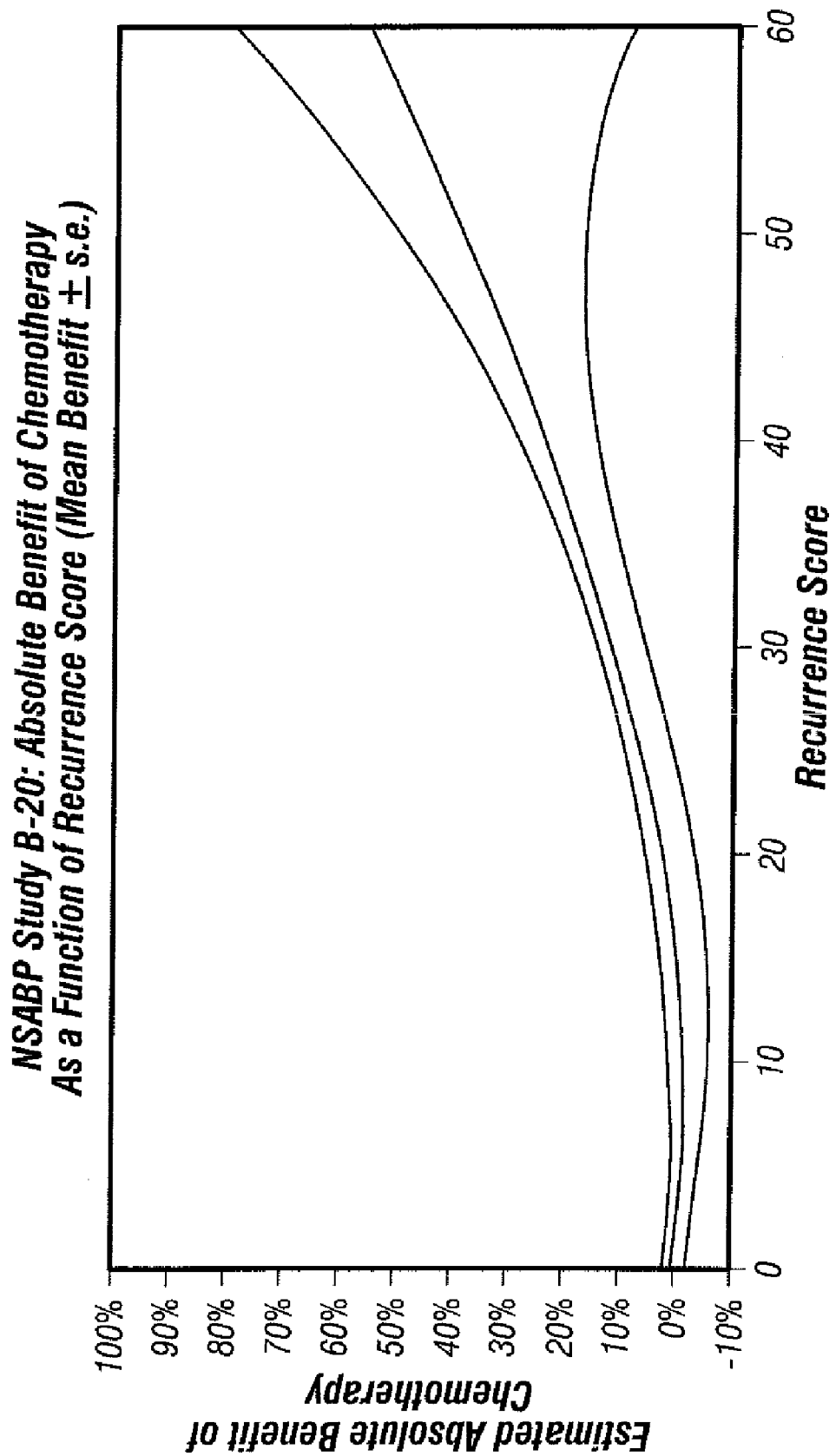
FIG. 2 shows the absolute benefit of chemotherapy as determined by DRFS at 10 years within NSABP B-20 patient groups identified by Recurrence Score as a continuous variable.

Because the RS is a continuous variable the precise numerical RS for a given patient can be used to indicate that patient's individual likelihood of benefit from chemotherapy. This is shown by FIG. 2.

All references cited throughout the disclosure are hereby expressly incorporated by reference.

One skilled in the art will recognize numerous methods and materials similar or equivalent to those described herein, which could be used in the practice of the present invention. Indeed, the present invention is in no way limited to the methods and materials described. While the present invention has been described with reference to what are considered to be the specific embodiments, it is to be understood that the invention is not limited to such embodiments. To the contrary, the invention is intended to cover various modifications and equivalents included within the spirit and scope of the appended claims. For example, while the disclosure is illustrated by identifying genes and groups of genes useful in predicting the beneficial response of a breast cancer patient to treatment with CMF (cyclophosphamide, methotrexate, fluorouracil) chemotherapy similar methods to determine patient response to treatment with other chemotherapeutic drugs, as well as similar genes, gene sets and methods concerning other types of cancer are specifically within the scope herein.

TABLE 3

| Reagent | Gene | Accession | Oligo | Sequence | Length |
|---|---|---|---|---|---|
| Forward | ACTB | NM_001101 | S0034/B-acti.f2 | CAGCAGATGTGGATCAGCAAG | 21 |
| Reverse | ACTB | NM_001101 | S0036/B-acti.r2 | GCATTTGCGGTGGACGAT | 18 |
| Probe | ACTB | NM_001101 | S4730/B-acti.p2 | AGGAGTATGACGAGTCCGGCCCC | 23 |
| Forward | BAG1 | NM_004323 | S1386/BAG1.f2 | CGTTGTCAGCACTTGGAATACAA | 23 |
| Reverse | BAG1 | NM_004323 | S1387/BAG1.r2 | GTTCAACCTCTTCCTGTGGACTGT | 24 |
| Probe | BAG1 | NM_004323 | S4731/BAG1.p2 | CCCAATTAACATGACCCGGCAACCAT | 26 |
| Forward | BCL2 | NM_000633 | S0043/Bcl2.f2 | CAGATGGACCTAGTACCCACTGAGA | 25 |
| Reverse | BCL2 | NM_000633 | S0045/Bcl2.r2 | CCTATGATTTAAGGGCATTTTTCC | 24 |
| Probe | BCL2 | NM_000633 | S4732/Bcl2.p2 | TTCCACGCCGAAGGACAGCGAT | 22 |
| Forward | CONB1 | NM_031966 | S1720/CCNB1.f2 | TTCAGGTTGTTGCAGGAGAC | 20 |
| Reverse | CCNB1 | NM_031966 | S1721/CCNB1.r2 | CATCTTCTTGGGCACACAAT | 20 |
| Probe | CONB1 | NM_031966 | S4733/CCNB1.p2 | TGTCTCCATTATTGATCGGTTCATGCA | 27 |
| Forward | CD68 | NM_001251 | S0067/CD68.f2 | TGGTTCCCAGCCCTGTGT | 18 |

TABLE 3-continued

| Reagent | Gene | Accession | Oligo | Sequence | Length |
|---|---|---|---|---|---|
| Reverse | CD68 | NM_001251 | S0069/CD68.r2 | CTCCTCCACCCTGGGTTGT | 19 |
| Probe | CD68 | NM_001251 | S4734/CD68.p2 | CTCCAAGCCCAGATTCAGATTCGAGTCA | 28 |
| Forward | SCUBE2 | NM_020974 | S1494/SCUBE2.f2 | TGACAATCAGCACACCTGCAT | 21 |
| Reverse | SCUBE2 | NM_020974 | S1495/SCUBE2.r2 | TGTGACTACAGCCGTGATCCTTA | 23 |
| Probe | SCUBE2 | NM_020974 | S4735/SCUBE2.p2 | CAGGCCCTCTTCCGAGCGGT | 20 |
| Forward | CTSL2 | NM_001333 | S4354/CTSL2.f1 | TGTCTCACTGAGCGAGCAGAA | 21 |
| Reverse | CTSL2 | NM_001333 | S4355/CTSL2.r1 | ACCATTGCAGCCCTGATTG | 19 |
| Probe | CTSL2 | NM_001333 | S4356/CTSL2.p1 | CTTGAGGACGCGAACAGTCCACCA | 24 |
| Forward | ESR1 | NM_000125 | S0115/EstR1.f1 | CGTGGTGCCCCTCTATGAC | 19 |
| Reverse | ESR1 | NM_000125 | S0117/EstR1.r1 | GGCTAGTGGGCGCATGTAG | 19 |
| Probe | ESR1 | NM_000125 | S4737/EstR1.p1 | CTGGAGATGCTGGACGCCC | 19 |
| Forward | GAPD | NM_002046 | S0374/GAPD.f1 | ATTCCACCCATGGCAAATTC | 20 |
| Reverse | GAPD | NM_002046 | S0375/GAPD.r1 | GATGGGATTTCCATTGATGACA | 22 |
| Probe | GAPD | NM_002046 | S4738/GAPD.p1 | CCGTTCTCAGCCTTGACGGTGC | 22 |
| Forward | GRB7 | NM_005310 | S0130/GRB7.f2 | CCATCTGCATCCATCTTGTT | 20 |
| Reverse | GRB7 | NM_005310 | S0132/GRB7.r2 | GGCCACCAGGGTATTATCTG | 20 |
| Probe | GRB7 | NM_005310 | S4726/GRB7.p2 | CTCCCCACCCTTGAGAAGTGCCT | 23 |
| Forward | GSTM1 | NM_000561 | S2026/GSTM1.r1 | GGCCCAGCTTGAATTTTTCA | 20 |
| Reverse | GSTM1 | NM_000561 | S2027/GSTM1.f1 | AAGCTATGAGGAAAAGAAGTACACGAT | 27 |
| Probe | GSTM1 | NM_000561 | S4739/GSTM1.p1 | TCAGCCACTGGCTTCTGTCATAATCAGGAG | 30 |
| Forward | GUSB | NM_000181 | S0139/GUS.f1 | CCCACTCAGTAGCCAAGTCA | 20 |
| Reverse | GUSB | NM_000181 | S0141/GUS.r1 | CACGCAGGTGGTATCAGTCT | 20 |
| Probe | GUSB | NM_000181 | S4740/GUS.p1 | TCAAGTAAACGGGCTGTTTTCCAAACA | 27 |
| Forward | ERBB2 | NM_004448 | S0142/HER2.f3 | CGGTGTGAGAAGTGCAGCAA | 20 |
| Reverse | ERBB2 | NM_004448 | S0144/HER2.r3 | CCTCTCGCAAGTGCTCCAT | 19 |
| Probe | ERBB2 | NM_004448 | S4729/HER2.p3 | CCAGACCATAGCACACTCGGGCAC | 24 |
| Forward | MKI67 | NM_002417 | S0436/MKI67.f2 | CGGACTTTGGGTGCGACTT | 19 |
| Reverse | MKI67 | NM_002417 | S0437/MKI67.r2 | TTACAACTCTTCCACTGGGACGAT | 24 |
| Probe | MKI67 | NM_002417 | S4741/MKI67.p2 | CCACTTGTCGAACCACCGCTCGT | 23 |
| Forward | MYBL2 | NM_002466 | S3270/MYBL2.f1 | GCCGAGATCGCCAAGATG | 18 |
| Reverse | MYBL2 | NM_002466 | S3271/MYBL2.r1 | CTTTTGATGGTAGAGTTCCAGTGATTC | 27 |
| Probe | MYBL2 | NM_002466 | S4742/MYBL2.p1 | CAGCATTGTCTGTCCTCCCTGGCA | 24 |
| Forward | PGR | NM_000926 | S1336/PR.f6 | GCATCAGGCTGTCATTATGG | 20 |
| Reverse | PGR | NM_000926 | S1337/PR.r6 | AGTAGTTGTGCTGCCCTTCC | 20 |
| Probe | PGR | NM_000926 | S4743/PR.p6 | TGTCCTTACCTGTGGGAGCTGTAAGGTC | 28 |
| Forward | RPLP0 | NM_001002 | S0256/RPLP0.f2 | CCATTCTATCATCAACGGGTACAA | 24 |
| Reverse | RPLP0 | NM_001002 | S0258/RPLP0.r2 | TCAGCAAGTGGGAAGGTGTAATC | 23 |
| Probe | RPLP0 | NM_001002 | S4744/RPLP0.p2 | TCTCCACAGACAAGGCCAGGACTCG | 25 |
| Forward | STK6 | NM_003600 | S0794/STK6.f2 | CATCTTCCAGGAGGACCACT | 20 |

TABLE 3-continued

| Reagent | Gene | Accession | Oligo | Sequence | Length |
|---|---|---|---|---|---|
| Reverse | STK6 | NM_003600 | S0795/STK6.r2 | TCCGACCTTCAATCATTTCA | 20 |
| Probe | STK6 | NM_003600 | S4745/STK6.p2 | CTCTGTGGCACCCTGGACTACCTG | 24 |
| Forward | MMP11 | NM_005940 | S2067/MMP11.f3 | CCTGGAGGCTGCAACATACC | 20 |
| Reverse | MMP11 | NM_005940 | S2068/MMP11.r3 | TACAATGGCTTTGGAGGATAGCA | 23 |
| Probe | MMP11 | NM_005940 | S4746/MMP11.p3 | ATCCTCCTGAAGCCCTTTTCGCAGC | 25 |
| Forward | BIRC5 | NM_001168 | S0259/BIRC5.f2 | TGTTTTGATTCCCGGGCTTA | 20 |
| Reverse | BIRC5 | NM_001168 | S0261/BIRC5.r2 | CAAAGCTGTCAGCTCTAGCAAAAG | 24 |
| Probe | BIRC5 | NM_001168 | S4747/BIRC5.p2 | TGCCTTCTTCCTCCCTCACTTCTCACCT | 28 |
| Forward | TFRC | NM_003234 | S1352/TFRC.f3 | GCCAACTGCTTTCATTTGTG | 20 |
| Reverse | TFRC | NM_003234 | S1353/TFRC.r3 | ACTCAGGCCCATTTCCTTTA | 20 |
| Probe | TFRC | NM_003234 | S4748/TFRC.p3 | AGGGATCTGAACCAATACAGAGCAGACA | 28 |

TABLE 4

| Gene | LocusLink | Sequence |
|---|---|---|
| ACTB | NM_001101 | CAGCAGATGTGGATCAGCAAGCAGGAGTATGACGAGTCCGGCCCCTCCATCGTCCACCGCAAATCC |
| BAG1 | NM_004323 | CGTTGTCAGCACTTGGAATACAAGATGGTTGCCGGGTCATGTTAATTGGGAAAAGAACAGTCCACAGGAAGAGGTTGAAC |
| BCL2 | NM_000633 | CAGATGGACCTAGTACCCACTGAGATTTCCACGCCGAAGGACAGCGATGGGAAAATGCCCTTAAATCATAGG |
| CCNB1 | NM_031966 | TTCAGGTTGTTGCAGGAGACCATGTACATGACTGTCTCCATTATTGATCGGTTCATGCAGAATAATTGTGTGCCCAAGAAGATG |
| CD6B | NM_001251 | TGGTTCCCAGCCCTGTGTCCACCTCCAAGCCCAGATTCAGATTCGAGTCATGTACACAACCCAGGGTGGAGGAG |
| SCUBE2 | NM_020974 | TGACAATCAGCACACCTGCATTCACCGCTCGGAAGAGGGCCTGAGCTGCATGAATAAGGATCACGGCTGTAGTCACA |
| CTSL2 | NM_001333 | TGTCTCACTGAGCGAGCAGAATCTGGTGGACTGTTCGCGTCCTGAAGGCAATCAGGGCTGCAATGGT |
| ESR1 | NM_000125 | CGTGGTGCCCCTCTATGACCTGCTGCTGGAGATGCTGGACGCCCACCGCCTACATGCGCCCACTAGCC |
| GAPD | NM_002046 | ATTCCACCCATGGCAAATTCCATGGCACCGTCAAGGCTGAGAACGGGAAGCTTGTCATCAATGGAAATCCCATC |
| GRB7 | NM_005310 | CCATCTGCATCCATCTTGTTTGGGCTCCCCACCCTTGAGAAGTGCCTCAGATAATACCCTGGTGGCC |
| GSTM1 | NM_000561 | AAGCTATGAGGAAAAGAAGTACACGATGGGGGACGCTCCTGATTATGACAGAAGCCAGTGGCTGAATGAAAAATTCAAGCTGGGCC |
| GUSB | NM_000181 | CCCACTCAGTAGCCAAGTCACAATGTTTGGAAAACAGCCCGTTTACTTGAGCAAGACTGATACCACCTGCGTG |
| ERBB2 | NM_004448 | CGGTGTGAGAAGTGCAGCAAGCCCTGTGCCCGAGTGTGCTATGGTCTGGGCATGGAGCACTTGCGAGAGG |
| MKI67 | NM_002417 | CGGACTTTGGGTGCGACTTGACGAGCGGTGGTTCGACAAGTGGCCTTGCGGGCCGGATCGTCCCAGTGGAAGAGTTGTAA |
| MYBL2 | NM_002466 | GCCGAGATCGCCAAGATGTTGCCAGGGAGGACAGACAATGCTGTGAAGAATCACTGGAACTCTACCATCAAAAG |
| PGR | NM_000926 | GCATCAGGCTGTCATTATGGTGTCCTTACCTGTGGGAGCTGTAAGGTCTTCTTTAAGAGGGCAATGGAAGGGCAGCACAACTACT |
| RPLP0 | NM_001002 | CCATTCTATCATCAACGGGTACAAACGAGTCCTGGCCTTGTCTGTGGAGACGGATTACACCTTCCCACTTGCTGA |
| STK6 | NM_003600 | CATCTTCCAGGAGGACCACTCTCTGTGGCACCCTGGACTACCTGCCCCCTGAAATGATTGAAGGTCGGA |
| MMP11 | NM_005940 | CCTGGAGGCTGCAACATACCTCAATCCTGTCCCAGGCCGGATCCTCCTGAAGCCCTTTTCGCAGCACTGCTATCCTCCAAAGCCATTGTA |
| BIRC5 | NM_001168 | TGTTTTGATTCCCGGGCTTACCAGGTGAGAAGTGAGGGAGGAAGAAGGCAGTGTCCCTTTTGCTAGAGCTGACAGCTTTG |
| TFRC | NM_003234 | GCCAACTGCTTTCATTTGTGAGGGATCTGAACCAATACAGAGCAGACATAAAGGAAATGGGCCTGAGT |

What is claimed:

1. A method for determining a likelihood that a breast cancer patient will have a beneficial response to treatment with chemotherapy, comprising:
   measuring expression levels of RNA transcripts of at least two genes selected from BIRC5, MKi67, MYBL2, CCNB1, STK6, MMP11, SCUBE2, ERBB2, GRB7, ESR1, PGR, BCL2, CTSL2, GSTM1, CD68, and BAG1 in a biological sample obtained from a breast tumor of the patient;
   calculating a risk score (RS) based on said expression levels, wherein said expression levels comprise one or more of the following variables:
   (i) Recurrence Score;
   (ii) ESR1 Group Score;
   (iii) Invasion Group Score;
   (iv) Proliferation Group Score;
   (v) MYBL2 expression level; and
   (vi) SCUBE2 expression level,
      wherein each group score, MYBL2 expression level, and SCUBE2 expression level is weighted by its respective contribution to chemotherapy benefit,
      wherein the Recurrence Score, the Proliferation Group Score, the Invasion Group Score, and the MYBL2 expression level are positively correlated with the likelihood that the patient will have a beneficial response to chemotherapy, and
      wherein the ESR1 Group Score and the SCUBE2 expression level is negatively associated with the likelihood that the patient will have a beneficial response to chemotherapy; and
   creating a report based on the RS, comprising an estimate of the likelihood that the patient will have a beneficial response to chemotherapy.

2. The method of claim 1, wherein said treatment is administered as adjuvant chemotherapy.

3. The method of claim 1, wherein said chemotherapy comprises an anthracycline-based therapy.

4. The method of claim 3 wherein said anthracycline-based therapy is doxorubicin or adriamycin.

5. The method of claim 1, wherein said chemotherapy comprises a taxane derivative.

6. The method of claim 5 wherein said taxane derivative is paclitaxel or docetaxel.

7. The method of claim 1, wherein said chemotherapy comprises a topoisomerase inhibitor.

8. The method of claim 7 wherein said topoisomerase inhibitor is selected from the group consisting of camptothecin, topotecan, irinotecan, 20-S camptothecin, 9-nitro-camptothecin, 9-amino-camptothecin and GI147211.

9. The method of claim 1, wherein said chemotherapy comprises an inhibitor of nucleotide biosynthesis.

10. The method of claim 9, wherein said inhibitor of nucleotide biosynthesis is methotrexate and/or 5-fluorouracil (5-FU).

11. The method of claim 1, wherein said biological sample is fixed, paraffin-embedded, fresh, or frozen.

12. The method of claim 11 where the biological sample is from fine needle biopsy or core biopsy.

13. The method of claim 1, wherein measurement of said expression levels includes quantitative reverse transcription polymerase chain reaction (RT-PCR).

14. The method of claim 1, wherein the expression levels of the RNA transcripts are normalized relative to the expression levels of at least one reference gene, or its expression product.

15. The method of claim 14, wherein the at least one reference gene is selected from the group consisting of ACTB, GAPD, GUSB, RPLPO, and TFRC.

16. The method of claim 14, wherein the breast tumor sample is ESR1-positive.

17. The method of claim 1, further comprising:
   applying a threshold to the Proliferation Group Score to obtain a Proliferation Group Threshold Score, wherein the Proliferation Group Threshold Score equals 6.5, if the Proliferation Group Score is less than 6.5; and equals the Proliferation Group Score, if the Proliferation Group Score is greater than or equal to 6.5.

18. The method of claim 17, wherein the ESR1 Group Score and SCUBE2 expression level are weighted by a factor of 0.34; the Proliferation Group Threshold Score and MYBL2 expression level by a factor of 1.04; and the Invasion Group Score by a factor of 0.10.

19. A method of preparing a personalized genomics profile for a human subject diagnosed with breast cancer, comprising
   assaying, in a biological sample comprising a breast tumor sample obtained from said subject, expression levels of RNA transcripts of at least two genes selected from BIRC5, MKi67, MYBL2, CCNB1, STK6, MMP11, SCUBE2, ERBB2, GRB7, ESR1, PGR, BCL2, CTSL2, GSTM1, CD68, and BAG1;
   calculating a risk score (RS) based on said expression levels, wherein said expression levels comprise one or more of the following variables:
   (i) Recurrence Score;
   (ii) ESR1 Group Score;
   (iii) Invasion Group Score;
   (iv) Proliferation Group Score;
   (v) MYBL2 expression level; and
   (vi) SCUBE2 expression level,
      wherein each group score, the MYBL2 expression level, and the SCUBE2 expression level is weighted by its respective contribution to chemotherapy benefit,
      wherein the Recurrence Score, the Proliferation Group Score, the Invasion Group Score, and the MYBL2 expression level are positively correlated with the likelihood that the patient will have a beneficial response to chemotherapy, and wherein the ESR1 Group Score and the SCUBE2 expression level is negatively associated with the likelihood that the patient will have a beneficial response to chemotherapy; and creating a report based on the RS, comprising an estimate of the likelihood that the patient will have a beneficial response to chemotherapy.

20. The method of claim 19, wherein said expression levels used to calculate said variables are normalized relative to expression levels of at least one reference gene, or its expression product.

21. The method of claim 20, wherein the at least one reference gene is selected from the group consisting of ACTB, GAPD, GUSB, RPLPO, and TFRC.

22. The method of claim 19, wherein the breast tumor sample is ESR1-positive.

23. The method of claim 1, further comprising:

applying a threshold to the Proliferation Group Score to obtain a Proliferation Group Threshold Score, wherein the Proliferation Group Threshold Score equals 6.5, if the Proliferation Group Score is less than 6.5; and equals the Proliferation Group Score, if the Proliferation Group Score is greater than or equal to 6.5.

24. The method of claim 23, wherein the ESR1 Group Score and SCUBE2 expression level are weighted by a factor of 0.34; the Proliferation Group Threshold Score and MYBL2 expression level by a factor of 1.04; and the Invasion Group Score by a factor of 0.10.

* * * * *

SEQUENCE LISTING

<160> NUMBER OF SEQ ID NOS: 84

<210> SEQ ID NO 1
<211> LENGTH: 21
<212> TYPE: DNA
<213> ORGANISM: Artificial Sequence
<220> FEATURE:
<223> OTHER INFORMATION: Synthetic Oligonucleotide Forward Primer

<400> SEQUENCE: 1
cagcagatgt ggatcagcaa g                                        21

<210> SEQ ID NO 2
<211> LENGTH: 18
<212> TYPE: DNA
<213> ORGANISM: Artificial Sequence
<220> FEATURE:
<223> OTHER INFORMATION: Synthetic Oligonucleotide Reverse Primer

<400> SEQUENCE: 2
gcatttgcgg tggacgat                                            18

<210> SEQ ID NO 3
<211> LENGTH: 23
<212> TYPE: DNA
<213> ORGANISM: Artificial Sequence
<220> FEATURE:
<223> OTHER INFORMATION: Synthetic Oligonucleotide Probe

<400> SEQUENCE: 3
aggagtatga cgagtccggc ccc                                      23

<210> SEQ ID NO 4
<211> LENGTH: 23
<212> TYPE: DNA
<213> ORGANISM: Artificial Sequence
<220> FEATURE:
<223> OTHER INFORMATION: Synthetic Oligonucleotide Forward Primer

<400> SEQUENCE: 4
cgttgtcagc acttggaata caa                                      23

<210> SEQ ID NO 5
<211> LENGTH: 24
<212> TYPE: DNA
<213> ORGANISM: Artificial Sequence
<220> FEATURE:
<223> OTHER INFORMATION: Synthetic Oligonucleotide Reverse Primer

<400> SEQUENCE: 5
gttcaacctc ttcctgtgga ctgt                                     24

<210> SEQ ID NO 6
<211> LENGTH: 26
<212> TYPE: DNA
<213> ORGANISM: Artificial Sequence
<220> FEATURE:
<223> OTHER INFORMATION: Synthetic Oligonucleotide Probe

<400> SEQUENCE: 6
cccaattaac atgacccggc aaccat                                   26

<210> SEQ ID NO 7
<211> LENGTH: 25
<212> TYPE: DNA

```
<213> ORGANISM: Artificial Sequence
<220> FEATURE:
<223> OTHER INFORMATION: Synthetic Oligonucleotide Forward Primer

<400> SEQUENCE: 7
cagatggacc tagtacccac tgaga                                              25

<210> SEQ ID NO 8
<211> LENGTH: 24
<212> TYPE: DNA
<213> ORGANISM: Artificial Sequence
<220> FEATURE:
<223> OTHER INFORMATION: Synthetic Oligonucleotide Reverse Primer

<400> SEQUENCE: 8
cctatgattt aagggcattt ttcc                                               24

<210> SEQ ID NO 9
<211> LENGTH: 22
<212> TYPE: DNA
<213> ORGANISM: Artificial Sequence
<220> FEATURE:
<223> OTHER INFORMATION: Synthetic Oligonucleotide Probe

<400> SEQUENCE: 9
ttccacgccg aaggacagcg at                                                 22

<210> SEQ ID NO 10
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 10
ttcaggttgt tgcaggagac                                                    20

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 11
catcttcttg ggcacacaat                                                    20

<210> SEQ ID NO 12
<211> LENGTH: 27
<212> TYPE: DNA
<213> ORGANISM: Artificial Sequence
<220> FEATURE:
<223> OTHER INFORMATION: Synthetic Oligonucleotide Probe

<400> SEQUENCE: 12
tgtctccatt attgatcggt tcatgca                                            27

<210> SEQ ID NO 13
<211> LENGTH: 18
<212> TYPE: DNA
<213> ORGANISM: Artificial Sequence
<220> FEATURE:
<223> OTHER INFORMATION: Synthetic Oligonucleotide Forward Primer

<400> SEQUENCE: 13
tggttcccag ccctgtgt                                                      18
```

<210> SEQ ID NO 14
<211> LENGTH: 19
<212> TYPE: DNA
<213> ORGANISM: Artificial Sequence
<220> FEATURE:
<223> OTHER INFORMATION: Synthetic Oligonucleotide Reverse Primer

<400> SEQUENCE: 14
ctcctccacc ctgggttgt                                              19

<210> SEQ ID NO 15
<211> LENGTH: 28
<212> TYPE: DNA
<213> ORGANISM: Artificial Sequence
<220> FEATURE:
<223> OTHER INFORMATION: Synthetic Oligonucleotide Probe

<400> SEQUENCE: 15
ctccaagccc agattcagat tcgagtca                                    28

<210> SEQ ID NO 16
<211> LENGTH: 21
<212> TYPE: DNA
<213> ORGANISM: Artificial Sequence
<220> FEATURE:
<223> OTHER INFORMATION: Synthetic Oligonucleotide Forward Primer

<400> SEQUENCE: 16
tgacaatcag cacacctgca t                                           21

<210> SEQ ID NO 17
<211> LENGTH: 23
<212> TYPE: DNA
<213> ORGANISM: Artificial Sequence
<220> FEATURE:
<223> OTHER INFORMATION: Synthetic Oligonucleotide Reverse Primer

<400> SEQUENCE: 17
tgtgactaca gccgtgatcc tta                                         23

<210> SEQ ID NO 18
<211> LENGTH: 20
<212> TYPE: DNA
<213> ORGANISM: Artificial Sequence
<220> FEATURE:
<223> OTHER INFORMATION: Synthetic Oligonucleotide Probe

<400> SEQUENCE: 18
caggccctct tccgagcggt                                             20

<210> SEQ ID NO 19
<211> LENGTH: 21
<212> TYPE: DNA
<213> ORGANISM: Artificial Sequence
<220> FEATURE:
<223> OTHER INFORMATION: Synthetic Oligonucleotide Forward Primer

<400> SEQUENCE: 19
tgtctcactg agcgagcaga a                                           21

<210> SEQ ID NO 20
<211> LENGTH: 19
<212> TYPE: DNA
<213> ORGANISM: Artificial Sequence
<220> FEATURE:
<223> OTHER INFORMATION: Synthetic Oligonucleotide Reverse Primer -continued

```
<400> SEQUENCE: 20
accattgcag ccctgattg                                                    19

<210> SEQ ID NO 21
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 21
cttgaggacg cgaacagtcc acca                                              24

<210> SEQ ID NO 22
<211> LENGTH: 19
<212> TYPE: DNA
<213> ORGANISM: Artificial Sequence
<220> FEATURE:
<223> OTHER INFORMATION: Synthetic Oligonucleotide Forward Primer

<400> SEQUENCE: 22
cgtggtgccc ctctatgac                                                    19

<210> SEQ ID NO 23
<211> LENGTH: 19
<212> TYPE: DNA
<213> ORGANISM: Artificial Sequence
<220> FEATURE:
<223> OTHER INFORMATION: Synthetic Oligonucleotide Reverse Primer

<400> SEQUENCE: 23
ggctagtggg cgcatgtag                                                    19

<210> SEQ ID NO 24
<211> LENGTH: 19
<212> TYPE: DNA
<213> ORGANISM: Artificial Sequence
<220> FEATURE:
<223> OTHER INFORMATION: Synthetic Oligonucleotide Probe

<400> SEQUENCE: 24
ctggagatgc tggacgccc                                                    19

<210> SEQ ID NO 25
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 25
attccaccca tggcaaattc                                                   20

<210> SEQ ID NO 26
<211> LENGTH: 22
<212> TYPE: DNA
<213> ORGANISM: Artificial Sequence
<220> FEATURE:
<223> OTHER INFORMATION: Synthetic Oligonucleotide Reverse Primer

<400> SEQUENCE: 26
gatgggattt ccattgatga ca                                                22

<210> SEQ ID NO 27
<211> LENGTH: 22
<212> TYPE: DNA
```

<213> ORGANISM: Artificial Sequence
<220> FEATURE:
<223> OTHER INFORMATION: Synthetic Oligonucleotide Probe

<400> SEQUENCE: 27
ccgttctcag ccttgacggt gc                                                22

<210> SEQ ID NO 28
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 28
ccatctgcat ccatcttgtt                                                   20

<210> SEQ ID NO 29
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 29
ggccaccagg gtattatctg                                                   20

<210> SEQ ID NO 30
<211> LENGTH: 23
<212> TYPE: DNA
<213> ORGANISM: Artificial Sequence
<220> FEATURE:
<223> OTHER INFORMATION: Synthetic Oligonucleotide Probe

<400> SEQUENCE: 30 ctcccccaccc ttgagaagtg cct                                              23

<210> SEQ ID NO 31
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 31
ggcccagctt gaattttcta                                                   20

<210> SEQ ID NO 32
<211> LENGTH: 27
<212> TYPE: DNA
<213> ORGANISM: Artificial Sequence
<220> FEATURE:
<223> OTHER INFORMATION: Synthetic Oligonucleotide Reverse Primer

<400> SEQUENCE: 32
aagctatgag gaaaagaagt acacgat                                           27

<210> SEQ ID NO 33
<211> LENGTH: 30
<212> TYPE: DNA
<213> ORGANISM: Artificial Sequence
<220> FEATURE:
<223> OTHER INFORMATION: Synthetic Oligonucleotide Probe

<400> SEQUENCE: 33
tcagccactg gcttctgtca taatcaggag                                        30

<210> SEQ ID NO 34
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 34
cccactcagt agccaagtca                                              20

<210> SEQ ID NO 35
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 35
cacgcaggtg gtatcagtct                                              20

<210> SEQ ID NO 36
<211> LENGTH: 27
<212> TYPE: DNA
<213> ORGANISM: Artificial Sequence
<220> FEATURE:
<223> OTHER INFORMATION: Synthetic Oligonucleotide Probe

<400> SEQUENCE: 36
tcaagtaaac gggctgtttt ccaaaca                                      27

<210> SEQ ID NO 37
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 37
cggtgtgaga agtgcagcaa                                              20

<210> SEQ ID NO 38
<211> LENGTH: 19
<212> TYPE: DNA
<213> ORGANISM: Artificial Sequence
<220> FEATURE:
<223> OTHER INFORMATION: Synthetic Oligonucleotide Reverse Primer

<400> SEQUENCE: 38
cctctcgcaa gtgctccat                                               19

<210> SEQ ID NO 39
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 39
ccagaccata gcacactcgg gcac                                         24

<210> SEQ ID NO 40
<211> LENGTH: 19
<212> TYPE: DNA
<213> ORGANISM: Artificial Sequence
<220> FEATURE:
<223> OTHER INFORMATION: Synthetic Oligonucleotide Forward Primer

<400> SEQUENCE: 40
cggactttgg gtgcgactt                                                19

<210> SEQ ID NO 41
<211> LENGTH: 24
<212> TYPE: DNA
<213> ORGANISM: Artificial Sequence
<220> FEATURE:
<223> OTHER INFORMATION: Synthetic Oligonucleotide Reverse Primer

<400> SEQUENCE: 41
ttacaactct tccactggga cgat                                          24

<210> SEQ ID NO 42
<211> LENGTH: 23
<212> TYPE: DNA
<213> ORGANISM: Artificial Sequence
<220> FEATURE:
<223> OTHER INFORMATION: Synthetic Oligonucleotide Probe

<400> SEQUENCE: 42
ccacttgtcg aaccaccgct cgt                                           23

<210> SEQ ID NO 43
<211> LENGTH: 18
<212> TYPE: DNA
<213> ORGANISM: Artificial Sequence
<220> FEATURE:
<223> OTHER INFORMATION: Synthetic Oligonucleotide Forward Primer

<400> SEQUENCE: 43
gccgagatcg ccaagatg                                                 18

<210> SEQ ID NO 44
<211> LENGTH: 27
<212> TYPE: DNA
<213> ORGANISM: Artificial Sequence
<220> FEATURE:
<223> OTHER INFORMATION: Synthetic Oligonucleotide Reverse Primer

<400> SEQUENCE: 44
cttttgatgg tagagttcca gtgattc                                       27

<210> SEQ ID NO 45
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 45
cagcattgtc tgtcctccct ggca                                          24

<210> SEQ ID NO 46
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 46
gcatcaggct gtcattatgg                                               20

<210> SEQ ID NO 47
<211> LENGTH: 20
<212> TYPE: DNA

```
<213> ORGANISM: Artificial Sequence
<220> FEATURE:
<223> OTHER INFORMATION: Synthetic Oligonucleotide Reverse Primer

<400> SEQUENCE: 47
agtagttgtg ctgcccttcc                                                    20

<210> SEQ ID NO 48
<211> LENGTH: 28
<212> TYPE: DNA
<213> ORGANISM: Artificial Sequence
<220> FEATURE:
<223> OTHER INFORMATION: Synthetic Oligonucleotide Probe

<400> SEQUENCE: 48
tgtccttacc tgtgggagct gtaaggtc                                           28

<210> SEQ ID NO 49
<211> LENGTH: 24
<212> TYPE: DNA
<213> ORGANISM: Artificial Sequence
<220> FEATURE:
<223> OTHER INFORMATION: Synthetic Oligonucleotide Forward Primer

<400> SEQUENCE: 49
ccattctatc atcaacgggt acaa                                               24

<210> SEQ ID NO 50
<211> LENGTH: 23
<212> TYPE: DNA
<213> ORGANISM: Artificial Sequence
<220> FEATURE:
<223> OTHER INFORMATION: Synthetic Oligonucleotide Reverse Primer

<400> SEQUENCE: 50
tcagcaagtg ggaaggtgta atc                                                23

<210> SEQ ID NO 51
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 51
tctccacaga caaggccagg actcg                                              25

<210> SEQ ID NO 52
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 52
catcttccag gaggaccact                                                    20

<210> SEQ ID NO 53
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 53
tccgaccttc aatcatttca                                                    20
```

```
<210> SEQ ID NO 54
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 54
ctctgtggca ccctggacta cctg                                              24

<210> SEQ ID NO 55
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 55
cctggaggct gcaacatacc                                                   20

<210> SEQ ID NO 56
<211> LENGTH: 23
<212> TYPE: DNA
<213> ORGANISM: Artificial Sequence
<220> FEATURE:
<223> OTHER INFORMATION: Synthetic Oligonucleotide Reverse Primer

<400> SEQUENCE: 56
tacaatggct ttggaggata gca                                               23

<210> SEQ ID NO 57
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 57
atcctcctga agccctttc gcagc                                              25

<210> SEQ ID NO 58
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 58
tgttttgatt cccgggctta                                                   20

<210> SEQ ID NO 59
<211> LENGTH: 24
<212> TYPE: DNA
<213> ORGANISM: Artificial Sequence
<220> FEATURE:
<223> OTHER INFORMATION: Synthetic Oligonucleotide Reverse Primer

<400> SEQUENCE: 59
caaagctgtc agctctagca aaag                                              24

<210> SEQ ID NO 60
<211> LENGTH: 28
<212> TYPE: DNA
<213> ORGANISM: Artificial Sequence
<220> FEATURE:
<223> OTHER INFORMATION: Synthetic Oligonucleotide Probe
```

```
-continued

<400> SEQUENCE: 60
tgccttcttc ctccctcact tctcacct                                        28

<210> SEQ ID NO 61
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 61
gccaactgct ttcatttgtg                                                 20

<210> SEQ ID NO 62
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 62
actcaggccc atttccttta                                                 20

<210> SEQ ID NO 63
<211> LENGTH: 28
<212> TYPE: DNA
<213> ORGANISM: Artificial Sequence
<220> FEATURE:
<223> OTHER INFORMATION: Synthetic Oligonucleotide Probe

<400> SEQUENCE: 63
agggatctga accaatacag agcagaca                                        28

<210> SEQ ID NO 64
<211> LENGTH: 66
<212> TYPE: DNA
<213> ORGANISM: Artificial Sequence
<220> FEATURE:
<223> OTHER INFORMATION: Amplicon Sequence

<400> SEQUENCE: 64
cagcagatgt ggatcagcaa gcaggagtat gacgagtccg gcccctccat cgtccaccgc     60
aaatgc                                                                66

<210> SEQ ID NO 65
<211> LENGTH: 81
<212> TYPE: DNA
<213> ORGANISM: Artificial Sequence
<220> FEATURE:
<223> OTHER INFORMATION: Amplicon Sequence

<400> SEQUENCE: 65
cgttgtcagc acttggaata caagatggtt gccgggtcat gttaattggg aaaagaaca     60 gtccacagga agaggttgaa c                                               81

<210> SEQ ID NO 66
<211> LENGTH: 73
<212> TYPE: DNA
<213> ORGANISM: Artificial Sequence
<220> FEATURE:
<223> OTHER INFORMATION: Amplicon Sequence

<400> SEQUENCE: 66
cagatggacc tagtacccac tgagatttcc acgccgaagg acagcgatgg gaaaatgcc     60
```
cttaaatcat agg                                                      73

<210> SEQ ID NO 67
<211> LENGTH: 84
<212> TYPE: DNA
<213> ORGANISM: Artificial Sequence
<220> FEATURE:
<223> OTHER INFORMATION: Amplicon Sequence

<400> SEQUENCE: 67
ttcaggttgt tgcaggagac catgtacatg actgtctcca ttattgatcg gttcatgcag    60
aataattgtg tgcccaagaa gatg                                          84

<210> SEQ ID NO 68
<211> LENGTH: 74
<212> TYPE: DNA
<213> ORGANISM: Artificial Sequence
<220> FEATURE:
<223> OTHER INFORMATION: Amplicon Sequence

<400> SEQUENCE: 68
tggttcccag ccctgtgtcc acctccaagc ccagattcag attcgagtca tgtacacaac    60
ccagggtgga ggag                                                     74

<210> SEQ ID NO 69
<211> LENGTH: 77
<212> TYPE: DNA
<213> ORGANISM: Artificial Sequence
<220> FEATURE:
<223> OTHER INFORMATION: Amplicon Sequence

<400> SEQUENCE: 69
tgacaatcag cacacctgca ttcaccgctc ggaagagggc ctgagctgca tgaataagga    60
tcacggctgt agtcaca                                                  77

<210> SEQ ID NO 70
<211> LENGTH: 67
<212> TYPE: DNA
<213> ORGANISM: Artificial Sequence
<220> FEATURE:
<223> OTHER INFORMATION: Amplicon Sequence

<400> SEQUENCE: 70
tgtctcactg agcgagcaga atctggtgga ctgttcgcgt cctcaaggca atcagggctg    60
caatggt                                                             67

<210> SEQ ID NO 71
<211> LENGTH: 68
<212> TYPE: DNA
<213> ORGANISM: Artificial Sequence
<220> FEATURE:
<223> OTHER INFORMATION: Amplicon Sequence

<400> SEQUENCE: 71
cgtggtgccc ctctatgacc tgctgctgga gatgctggac gcccaccgcc tacatgcgcc    60
cactagcc                                                            68

<210> SEQ ID NO 72
<211> LENGTH: 74
<212> TYPE: DNA
<213> ORGANISM: Artificial Sequence
<220> FEATURE:
<223> OTHER INFORMATION: Amplicon Sequence

```
<400> SEQUENCE: 72
attccaccca tggcaaattc catggcaccg tcaaggctga gaacgggaag cttgtcatca        60
atggaaatcc catc                                                         74

<210> SEQ ID NO 73
<211> LENGTH: 67
<212> TYPE: DNA
<213> ORGANISM: Artificial Sequence
<220> FEATURE:
<223> OTHER INFORMATION: Amplicon Sequence

<400> SEQUENCE: 73
ccatctgcat ccatcttgtt tgggctcccc acccttgaga agtgcctcag ataatccct        60 ggtggcc                                                                 67

<210> SEQ ID NO 74
<211> LENGTH: 86
<212> TYPE: DNA
<213> ORGANISM: Artificial Sequence
<220> FEATURE:
<223> OTHER INFORMATION: Amplicon Sequence

<400> SEQUENCE: 74
aagctatgag gaaagaagt acacgatggg ggacgctcct gattatgaca gaagccagtg        60
gctgaatgaa aaattcaagc tgggcc                                            86

<210> SEQ ID NO 75
<211> LENGTH: 73
<212> TYPE: DNA
<213> ORGANISM: Artificial Sequence
<220> FEATURE:
<223> OTHER INFORMATION: Amplicon Sequence

<400> SEQUENCE: 75
cccactcagt agccaagtca caatgtttgg aaaacagccc gtttacttga gcaagactga        60
taccacctgc gtg                                                          73

<210> SEQ ID NO 76
<211> LENGTH: 70
<212> TYPE: DNA
<213> ORGANISM: Artificial Sequence
<220> FEATURE:
<223> OTHER INFORMATION: Amplicon Sequence

<400> SEQUENCE: 76
cggtgtgaga agtgcagcaa gccctgtgcc cgagtgtgct atggtctggg catggagcac        60
ttgcgagagg                                                              70

<210> SEQ ID NO 77
<211> LENGTH: 80
<212> TYPE: DNA
<213> ORGANISM: Artificial Sequence
<220> FEATURE:
<223> OTHER INFORMATION: Amplicon Sequence

<400> SEQUENCE: 77
cggactttgg gtgcgacttg acgagcggtg gttcgacaag tggccttgcg ggccggatcg        60
tcccagtgga agagttgtaa                                                   80

<210> SEQ ID NO 78
<211> LENGTH: 74
<212> TYPE: DNA
```

```
<213> ORGANISM: Artificial Sequence
<220> FEATURE:
<223> OTHER INFORMATION: Amplicon Sequence

<400> SEQUENCE: 78
gccgagatcg ccaagatgtt gccagggagg acagacaatg ctgtgaagaa tcactggaac    60
tctaccatca aaag                                                      74

<210> SEQ ID NO 79
<211> LENGTH: 85
<212> TYPE: DNA
<213> ORGANISM: Artificial Sequence
<220> FEATURE:
<223> OTHER INFORMATION: Amplicon Sequence

<400> SEQUENCE: 79
gcatcaggct gtcattatgg tgtccttacc tgtgggagct gtaaggtctt ctttaagagg    60
gcaatggaag ggcagcacaa ctact                                          85

<210> SEQ ID NO 80
<211> LENGTH: 75
<212> TYPE: DNA
<213> ORGANISM: Artificial Sequence
<220> FEATURE:
<223> OTHER INFORMATION: Amplicon Sequence

<400> SEQUENCE: 80
ccattctatc atcaacgggt acaaacgagt cctggccttg tctgtggaga cggattacac    60
cttcccactt gctga                                                     75

<210> SEQ ID NO 81
<211> LENGTH: 69
<212> TYPE: DNA
<213> ORGANISM: Artificial Sequence
<220> FEATURE:
<223> OTHER INFORMATION: Amplicon Sequence

<400> SEQUENCE: 81
catcttccag gaggaccact ctctgtggca ccctggacta cctgccccct gaaatgattg    60
aaggtcgga                                                            69

<210> SEQ ID NO 82
<211> LENGTH: 90
<212> TYPE: DNA
<213> ORGANISM: Artificial Sequence
<220> FEATURE:
<223> OTHER INFORMATION: Amplicon Sequence

<400> SEQUENCE: 82
cctggaggct gcaacatacc tcaatcctgt cccaggccgg atcctcctga agcccttttc    60
gcagcactgc tatcctccaa agccattgta                                     90

<210> SEQ ID NO 83
<211> LENGTH: 80
<212> TYPE: DNA
<213> ORGANISM: Artificial Sequence
<220> FEATURE:
<223> OTHER INFORMATION: Amplicon Sequence

<400> SEQUENCE: 83
tgttttgatt cccgggctta ccaggtgaga agtgagggag gaagaaggca gtgtcccttt    60
tgctagagct gacagctttg                                                80
```

```
<210> SEQ ID NO 84
<211> LENGTH: 68
<212> TYPE: DNA
<213> ORGANISM: Artificial Sequence
<220> FEATURE:
<223> OTHER INFORMATION: Amplicon Sequence

<400> SEQUENCE: 84
gccaactgct ttcatttgtg agggatctga accaatacag agcagacata aaggaaatgg       60
gcctgagt                                                                68
```